United States Patent
Magilavy

(10) Patent No.: US 9,730,930 B2
(45) Date of Patent: *Aug. 15, 2017

(54) TREATMENT FOR VITILIGO

(71) Applicant: Rigel Pharmaceuticals, Inc., South San Francisco, CA (US)

(72) Inventor: Daniel Magilavy, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,322

(22) Filed: May 18, 2015

(65) Prior Publication Data

US 2015/0246039 A1   Sep. 3, 2015

Related U.S. Application Data

(63) Continuation of application No. 14/025,609, filed on Sep. 12, 2013, now Pat. No. 9,034,881.

(60) Provisional application No. 61/700,153, filed on Sep. 12, 2012.

(51) Int. Cl.
  *A61K 31/505* (2006.01)
  *C07D 239/48* (2006.01)
  *A61K 45/06* (2006.01)
  *A61K 9/00* (2006.01)
  *A61K 47/10* (2017.01)
  A61K 31/145 (2006.01)
  A61K 31/506 (2006.01)

(52) U.S. Cl.
  CPC .......... *A61K 31/505* (2013.01); *A61K 9/0014* (2013.01); *A61K 9/0048* (2013.01); *A61K 45/06* (2013.01); *A61K 47/10* (2013.01); *C07D 239/48* (2013.01); A61K 31/145 (2013.01); A61K 31/506 (2013.01)

(58) Field of Classification Search
  CPC .......................... A61K 31/145; A61K 31/506
  USPC ....................................................... 514/256
  See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| D296,006 S | 5/1988 | Asche | |
| 5,008,110 A | 4/1991 | Benecke et al. | |
| 5,591,767 A | 1/1997 | Mohr et al. | |
| 5,683,712 A | 11/1997 | Cavazza | |
| 5,948,433 A | 9/1999 | Burton et al. | |
| 5,965,154 A | 10/1999 | Haralambopoulos | |
| 6,010,715 A | 1/2000 | Wick et al. | |
| 7,491,732 B2 | 2/2009 | Li et al. | |
| 7,812,029 B1 | 10/2010 | Singh et al. | |
| 7,915,273 B2 | 3/2011 | Argade et al. | |
| 8,053,434 B2 | 11/2011 | Ding et al. | |
| 8,193,197 B2 | 6/2012 | Li et al. | |
| 9,034,881 B2 * | 5/2015 | Magilavy | A61K 45/06 514/256 |
| 2007/0203161 A1 | 8/2007 | Argade et al. | |

FOREIGN PATENT DOCUMENTS

| | | |
|---|---|---|
| WO | WO 2006/133426 | 12/2006 |
| WO | WO 2007/077949 A1 | 7/2007 |
| WO | WO 2008/009458 A1 | 1/2008 |
| WO | WO 2011/017178 | 2/2011 |
| WO | WO 2011/097087 A1 | 8/2011 |
| WO | WO 2012/122452 | 9/2012 |

OTHER PUBLICATIONS

Boone et al., "Topical pimecrolimus in the treatment of vitiligo," *Eur. J. Dermatol.* 17(1):55-61, 2007.

Chang et al., "JAK3 Inhibition Significantly Attenuates Psoriasiform Skin Inflammation in DC18 Mutant PL/J Mice," *J. Immunol.* 183:2183-2192, 2009.

Moellmann et al., "Extracellular Granular Material and Degeneration of Keratinocytes in the Normally Pigmented Epidermis of Patents with Vitiligo," *J. Inv. Dermatol.*, 79:312-330, 1982.

Montes et al., "Value of histopathology in vitiligo," *Int. J. Dermatol.* 42(1):57-61, Jan. 2003.

Shi et al., "Understanding mechanisms of vitiligo development in Smyth line of chickens by transcriptomic microarray analysis of evolving autoimmune lesions," *BMC Immunol.* 13:18 (Apr. 2012).

Smith et al., "Reduction of phagosomes in the vitiligo (C57BL/6-mivit/mivit) mouse model of retinal degeneration," *Invest. Ophthalmol. & Vis. Sci.* 35(10):3625-3632, Sep. 1994.

(Continued)

*Primary Examiner* — Kevin E Weddington
(74) *Attorney, Agent, or Firm* — Travis Young; Klarquist Sparkman, LLP

(57) ABSTRACT

Compounds I and II, as well as prodrugs, hydrates, solvates, N-oxides, salts and pharmaceutical compositions containing them, are useful for treating vitiligo. In certain embodiments, the compounds are provided in topical compositions.

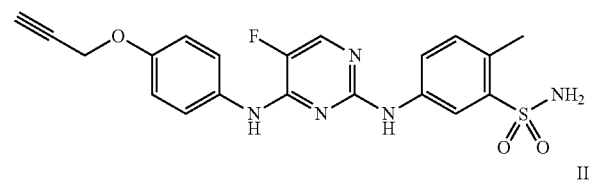

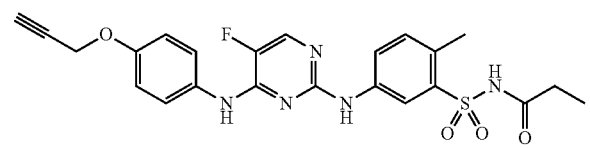

14 Claims, 2 Drawing Sheets

(56) References Cited

OTHER PUBLICATIONS

Stepicheva et al., "Abnormal morphology of melanosomes in the autoimmune vitiligo-prone Smith line chicken does not appear to be due to alternation of lipid composition," *J. Immunol.* 184:83.16, 2010.
Verma et al., "Inflammatory vitiligo with raised borders and psoriasiform histopathology," *Dermatology Online Journal* 11(3):13, 2005.
Wang et al., "Th17 Cells and Activated Dendritic Cells Are Increased in Vitiligo Lesions," *PLoS One* 6(4):e18907, 2011.
Balague et al., "Understanding autoimmune disease: new targets for drug discovery," *Drug Discovery Today* 14(19-20):926-934, Oct. 1, 2009.

\* cited by examiner

TREATMENT FOR VITILIGO

CROSS REFERENCE TO RELATED APPLICATION

This is a continuation of U.S. patent application Ser. No. 14/025,609, filed Sep. 12, 2013, which claims the benefit of U.S. Provisional Application No. 61/700,153, filed Sep. 12, 2012. These prior applications are incorporated herein by reference.

FIELD

The present disclosure relates to compounds, hydrates, solvates, prodrugs, salts, and N-oxides thereof, and pharmaceutical compositions comprising the compounds, and methods of using these compounds and compositions thereof in the treatment of vitiligo.

BACKGROUND

Vitiligo is a condition that causes depigmentation of skin, typically in sections or patches, and affects about 1-2% of the world population. Vitiligo occurs when there is an absence of functional melanocytes (melanin-producing cells) in the skin. Vitiligo also can affect the mucous membranes and the eye. There may be a genetic predisposition to vitiligo in some cases. The average age at vitiligo onset is about 20 years, with onset most commonly observed between the ages of 10 and 30.

Vitiligo occurs most often on the face and extremities—typically the hands and wrists. Depigmentation also can occur around the mouth, eyes, nostrils, genitalia, and umbilicus. Depigmented patches are flat areas of normal-feeling skin, and may have a hyperpigmented edge. The edges typically are well-defined but irregular. In trichrome vitiligo, there is an intermediate zone of hypochromia between the achromic center and peripheral unaffected skin.

There are several clinical classifications of vitiligo. Segmental vitiligo presents as one or more macules in a dermatomal or quasidermatomal pattern, and occurs most commonly in children. All other types of vitiligo are classified as non-segmental vitiligo, which is most common. Focal vitiligo is characterized by depigmentation in one area, or macule, such as the trigeminal nerve distribution. Other forms of non-segmental vitiligo often produce symmetric patches, sometimes covering large areas. Mucosal vitiligo affects only mucosal membranes. Generalized vitiligo may be acrofacial, in which depigmentation occurs on the distal fingers and periorificial areas, or vulgaris, which is characterized by widely distributed, scattered patches. Universal vitiligo manifests as complete or nearly complete depigmentation, and frequently is associated with multiple endocrinopathy syndrome. The exact cause of melanocyte loss in vitiligo remains debatable, but recent observations have pointed to a role for cellular immunity in the pathogenesis of vitiligo (see, for example, Wang et al. (2011) Th17 Cells and Activated Dendritic Cells Are Increased in Vitiligo Lesions. *PLoS ONE* 6(4): e18907). Despite some advances in elucidating the origins of the disorder, current therapies, such as topical corticosteroids, topical immunomodulators and psoralen phototherapy have serious side effects and limited therapeutic utility. Vitiligo is a disfiguring disease for which current therapies have proven unsatisfactory.

SUMMARY

Disclosed are compounds, prodrugs, corresponding salt forms, and methods of using these compounds, and solvates, prodrugs and salt forms thereof, that can be used to provide therapeutic benefit to subjects who have vitiligo or prophylactically for subjects who are at risk of developing vitiligo. For the purposes of brevity in description, for any embodiment where a compound is referred to specifically, the embodiment also includes hydrates, solvates, prodrugs, salt forms, and N-oxides of the compound, and/or a pharmaceutical composition containing the compound. The compounds may be administered by any suitable method, such as systemically, topically, or ocularly. In particular examples the compound is applied directly to depigmented areas of skin, for example in a topical formulation.

One embodiment provides a compound I:

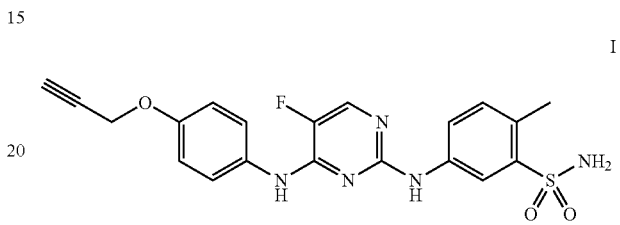

Another embodiment provides a particular prodrug of compound I, which is compound II:

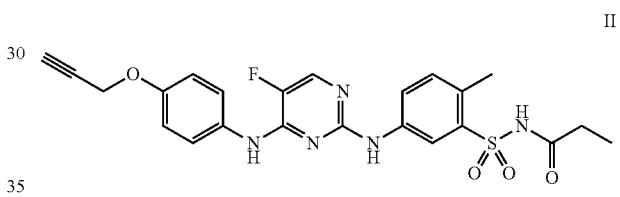

In one aspect, vitiligo is treated using an effective amount of compound I, compound II, and combinations thereof, and/or an effective amount of one or more pharmaceutical compositions that include the compound or compounds. One embodiment provides a method of treating vitiligo by administering to the subject an amount of compound I, compound II, or a combination thereof effective to treat vitiligo. In particular examples, the compound is administered in a topical formulation directly to depigmented skin, or localized areas including depigmented patches (e.g., the hands or face), without applying it to any substantial amount of unaffected skin.

In one aspect of the disclosed method, administration of one or more of the presently disclosed compounds is effective to cause at least partial regression, such as repigmentation of existing areas and/or reduced incidence of new areas, of the depigmented skin that characterize the disease. In another aspect of the disclosed method, administration of one or more of the disclosed compounds is effective to prevent vitiligo in a subject at risk of developing vitiligo.

In some examples, the subject is first determined to have vitiligo. For example, the subject displays one or more clinical and/or histopathological features of vitiligo. In another example, the subject is first determined to be at risk of developing vitiligo. For example, the subject may have a family history of vitiligo and be genetically at risk of developing vitiligo, and/or the subject may have a history of a disease associated with vitiligo, such as thyroid disease.

In another aspect, compound I, compound II, a combination thereof, or a composition comprising one or more of the compounds is administered either alone or in combination or adjunctively with one or more additional therapeutics, such as an anti-inflammatory, an antihistamine, an antibiotic, an antiviral, an emollient, an analgesic, systemic phototherapy, psoralen photochemotherapy, excimer laser therapy, thyroid hormone replacement medication, or any combination thereof.

In some examples, compound I, compound II, or a combination thereof is administered alone or with another biologically active agent in a topical sunscreen agent (to minimize the exposure to ultraviolet light that may worsen vitiligo, cause sunburn, or cause skin cancer of depigmented areas). Yet other combination treatments can include the use of concomitant or adjunctive treatment including those treatments described above.

Typically the disclosed compounds, when used for treating vitiligo, are administered at least once daily, such as at least two, three or four times daily, or are applied to the skin in a sustained release format (such as an adherent dispenser, for example a patch).

In another embodiment, a pharmaceutical formulation includes compound I and/or compound II, either in parent or salt form, and at least one pharmaceutically acceptable excipient, diluent, preservative, stabilizer, or mixtures thereof.

These and other embodiments are described in more detail below.

DETAILED DESCRIPTION

I. Abbreviations and Definitions

Figure 1:
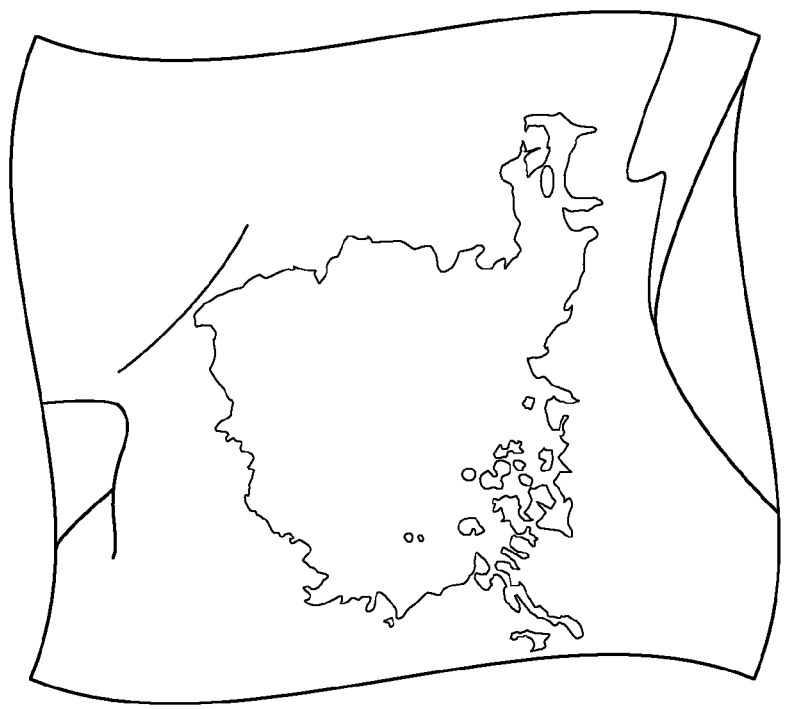
FIG. 1 is a prior art photograph that illustrates vitiligo on a subject's neck.
Figure 2:
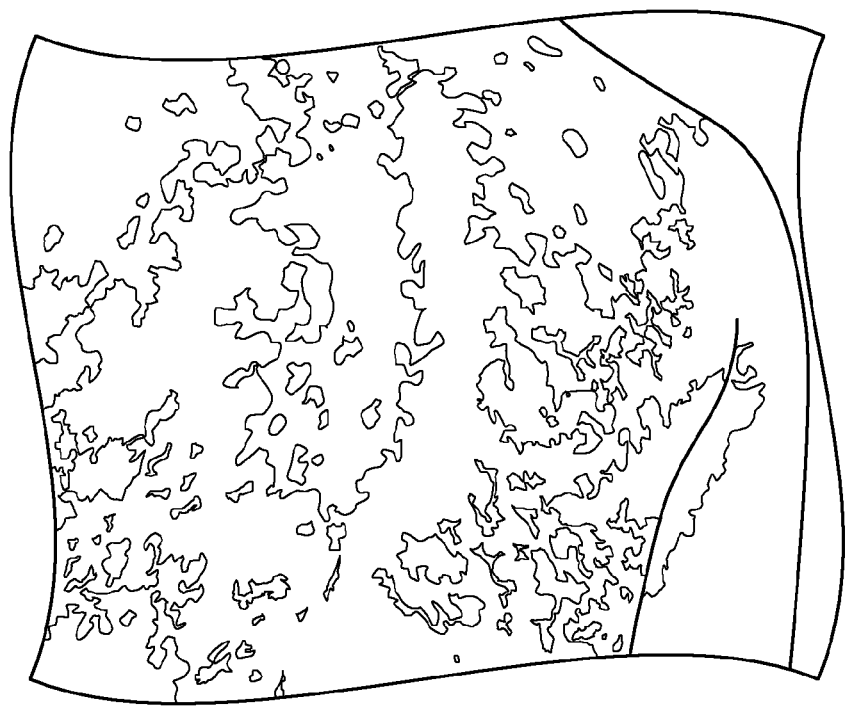
FIG. 2 is a prior art photograph that illustrates vitiligo on a subject's back.
Figure 3:
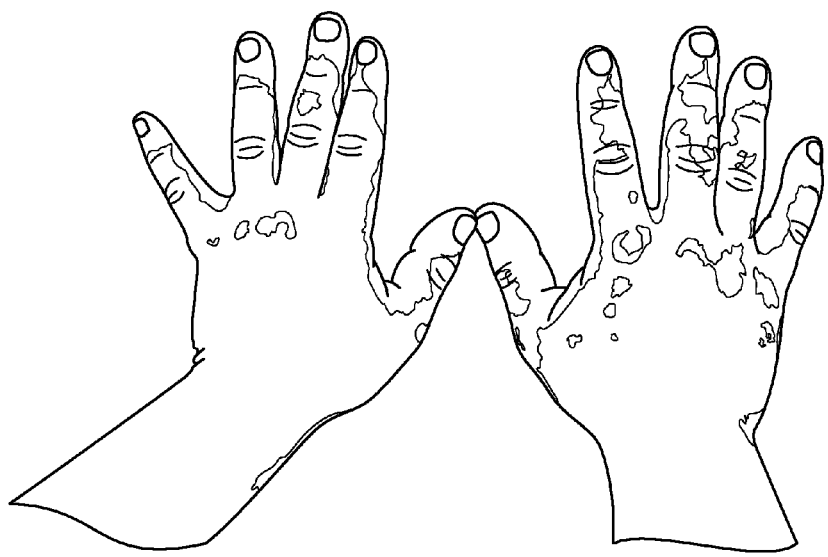
FIG. 3 is a prior art photograph that illustrates vitiligo on a subject's hands.

IL: Interleukin
JAK: Janus kinase
STAT: Signal transducer and activator of transcription
SYK: Spleen Tyrosine Kinase As used herein, the following definitions shall apply unless otherwise indicated.

"Corticosteroids" are steroid hormones that are produced in the adrenal cortex. Corticosteroids are involved in a wide range of physiologic systems such as stress response, immune response and regulation of inflammation, carbohydrate metabolism, protein catabolism, blood electrolyte levels, and behavior. Examples of corticosteroids include cortisol, prednisone and prednisolone. Corticosteroids can be administered either orally, parenterally (for example by injection) or by direct topical application to a lesion on the skin, and they may be combined with the compounds of formula I and/or II in a combination formulation. "Topical corticosteroids" are applied topically directly to the skin, but long term use of topical corticosteroids causes unsightly skin atrophy.

"Cutaneous" or "dermal" refers to the skin, which is the tissue forming the outer covering of the vertebrate body. The skin (which is also sometimes referred to as the "integumentary system"), in combination with the mucous membranes (particularly the oral, nasal, oral and eyelid membranes) help protect the body from its external environment. The skin consists of two layers (the dermis and epidermis), the outermost of which may be covered in many animals (including humans) at least in part with hair. It is mainly protective and sensory in function, along with the mucous membranes of the eye, nose and mouth.

"Epithelial surfaces" refers to tissue made up of epithelial cells that cover the surfaces of the body. Epithelial surfaces include external surfaces such as the skin and mucosa of the mouth and nose, as well as the linings of internal body surfaces. "External" epithelial surfaces are those exposed to the surfaces of the body (such as the skin, and the lining of the nose and mouth) and that are accessible to direct application of creams or ointments to the surface without the use of instrumentation (such as endoscopes or scalpels).

"Mucous membranes" (or "mucosa") are linings of mostly endodermal origin, covered in epithelium, which are involved in absorption and secretion. They line cavities that are exposed to the external environment and internal organs. They are continuous with skin at several locations, such as the nostrils, mouth, lips, eyelids, ears, genital area, and anus.

"Non-steroidal anti-inflammatory drug (NSAID)" is a type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate. These agents can be administered either orally, parenterally (for example by injection) or by direct topical application to an inflamed area, and they may be combined with the compounds of formula I and/or II in a combination formulation.

"N-oxide" refers to a compound including a nitrogen bearing an oxy radical.

"Pharmaceutically acceptable salt" refers to a biologically compatible salt of a compound that can be used as a drug, which salts are derived from a variety of organic and inorganic counter ions well known in the art.

"Pharmaceutically effective amount" or "therapeutically effective amount" refers to an amount of a compound sufficient to treat a specified disorder or disease or one or more of its symptoms and/or to prevent the occurrence of the disease or disorder. "Treatment" includes arresting further advancement of a disease, as well as reversing the disorder, inducing regression of lesions, or in some examples curing the disorder.

"Prodrug" refers to compounds that are transformed in vivo to yield the parent compound, for example, by hydrolysis in the gut or enzymatic conversion in blood. Common examples include, but are not limited to, ester and amide forms of a compound having an active form bearing a carboxylic acid moiety. Examples of pharmaceutically acceptable esters of the presently disclosed compounds include, but are not limited to, alkyl esters (for example with between about one and about six carbons) where the alkyl group is a straight or branched chain. Acceptable esters also include cycloalkyl esters and arylalkyl esters such as, but not limited to benzyl. Examples of pharmaceutically acceptable amides of the disclosed compounds include, but are not limited to, primary amides, and secondary and tertiary alkyl amides (for example with between about one and about six carbons). Amides and esters of the disclosed compounds can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in unsolvated as well as solvated forms with solvents, pharmaceutically acceptable or not, such as water, ethanol, and the like. Solvated forms of the presently disclosed compounds are contemplated herein and are encompassed by the invention, at least in generic terms.

"Subject" refers to humans and non-human subjects.

"Topical" delivery refers to application of a drug-containing formulation to the skin to directly treat cutaneous disorders or the cutaneous manifestations of a disease with the intent of substantially directing the pharmacological effect of the drug to the surface of the skin or within the skin. Topical dosage forms are typically semi-solid systems, but can include a variety of other dosage forms such as foams, sprays, medicated powders, solutions and medicated adhesive systems. Topical delivery includes external topical agents that are spread, sprayed, or otherwise dispersed on cutaneous tissues to cover the affected area, or internal topical agents that are applied to the mucous membranes orally, vaginally, or on anorectal tissues for local activity. The topical drugs disclosed herein can be administered in any topical dosage form, for example as a solid (powder, aerosol or plaster); liquid (lotion, liniment, solution, emulsion, suspension, aerosol) or semi-solid (ointment, cream, paste, gel, jelly or suppository).

As used herein, and as well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable.

"Vitiligo" is a condition characterized by loss of cutaneous melanocytes and/or abnormal melanocyte function.

II. Compounds

Disclosed are compounds, solvates, prodrugs, corresponding salt forms, and methods of using these compounds, hydrates, solvates, prodrugs and salt forms in the treatment and/or prevention of vitiligo. For the purposes of brevity in description, for any embodiment where compound I and compound II are referred to specifically, the embodiment also includes hydrates, solvates, prodrugs, salt forms, and N-oxides of the compound, and/or a pharmaceutical composition containing compound I and/or compound II.

Compounds I and II and pharmaceutical compositions containing them are described in more detail below. Compound I is also referred to as N2-(3-aminosulfonyl-4-methylphenyl)-5-fluoro-N4-[4-(prop-2-ynyloxy)phenyl]-2,4-pyrimidinediamine. Compound II is also referred to as 5-fluoro-N2-(4-methyl-3-propionylaminosulfonylphenyl)-N4-[4-(prop-2-ynyloxy)phenyl]-2,4-pyrimidinediamine.

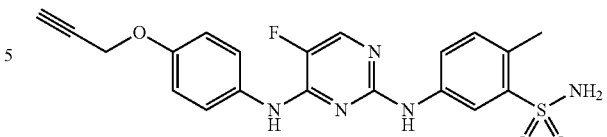

I

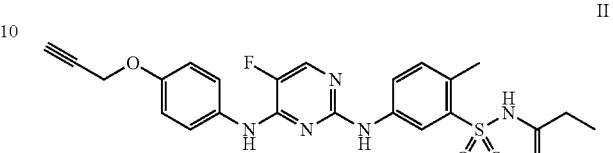

II

One of ordinary skill in the art will appreciate that compound II is a prodrug of compound I, and that compound II need not necessarily be pharmacologically inactive until converted into compound I, as currently understood. The mechanism by which the propionyl progroup metabolizes is not critical, and can be caused by, for example, hydrolysis under the acidic conditions of the stomach, and/or by enzymes present in the tissues and/or organs of the body, such as the skin, mucous membranes, saliva, tears, and including such enzymes as, for example, esterases, amidases, lipolases, phosphatases including ATPases and kinases, cytochrome P450's of the liver, and the like. In particular embodiments described herein, compounds I and/or II are used to treat vitiligo, and may therefore be administered directly to the skin. If an initially inactive prodrug is administered, it can be activated subsequent to administration, such as by enzymes (such as esterases) in the skin, or topically administered with another agent that activates the drug (for example, a reservoir of an activating substance in a patch, or an additional agent that is mixed with the prodrug prior to topical applications). In some embodiments, administration may include not only topical administration but also injection and the like, for example intradermal injection. Alternatively, these active agents may be administered systemically.

One of ordinary skill in the art will appreciate that compounds I and II may exist as tautomers, conformational isomers and/or geometric isomers. It should be understood that the disclosure encompasses any tautomeric, conformational isomeric and/or geometric isomeric forms of the compounds as well as mixtures of these various different isomeric forms.

Atropisomers are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation about bonds between the 2,4-pyrimidinediamine core structure and groups attached thereto or for example about bonds between the sulfonamide and the phenyl ring to which it is attached.

Compounds I and II may be in the form of salts. Such salts include salts suitable for pharmaceutical uses ("pharmaceutically-acceptable salts"), salts suitable for veterinary uses, etc. Such salts may be derived from acids or bases, as is well-known in the art. Exemplary salts described herein are sodium salts, potassium salts, arginine salts, choline salts and calcium salts, but generically any pharmaceutically acceptable salt may be used for methods described herein. Because compound I and compound II have both basic groups, for example pyrimidine nitrogens, and acidic groups, for example acidic protons on the sulfonamide and/or the nitrogens at N2 and N4 of the pyrimidinediamine system, these compounds can form pharmaceutically acceptable acid or base addition salts.

Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (for example, hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (for example, methanesulfonic acid, ethanesulfonic acid, 1,2-ethane-disulfonic acid, 2-hydroxyethanesulfonic acid, etc.), arylsulfonic acids (for example, benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid (xinafoic acid), salicylic acid, stearic acid, muconic acid, and the like.

Pharmaceutically acceptable salts also include salts formed when an acidic proton present in the parent compound is either replaced by a metal ion (for example, an alkali metal ion (e.g., sodium or potassium), an alkaline earth metal ion (e.g., calcium or magnesium), or an aluminum ion) or coordinates with an organic base (for example, ethanolamine, diethanolamine, triethanolamine, N-methylglucamine, morpholine, piperidine, dimethylamine, diethylamine, triethylamine, ammonia, etc.).

Salts of amine groups may comprise quaternary ammonium salts in which the amino nitrogen atom carries a suitable organic group such as an alkyl, alkenyl, alkynyl or aralkyl moiety.

The pharmaceutically acceptable salts described herein may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Compounds I and II, as well as the salts thereof, may also be in the form of solvates, for example hydrates, and N-oxides, as are well-known in the art.

III. Pharmaceutical Compositions

Pharmaceutical compositions comprising compounds I and II described herein can be manufactured by means of conventional mixing, dissolving, granulating, dragee-making, levigating, emulsifying, encapsulating, entrapping or lyophilization processes. The compositions can be formulated in a conventional manner using one or more physiologically acceptable carriers, diluents, excipients or auxiliaries which facilitate processing of the active compounds into preparations which can be used pharmaceutically, and particularly locally or topically.

Compounds I and II can be formulated in the pharmaceutical compositions per se, or in the form of a prodrug, hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed.

In one embodiment, a pharmaceutical formulation comprises compound I and/or compound II, and at least one pharmaceutically acceptable excipient, diluent, preservative, or stabilizer, or mixtures thereof. In one embodiment, the compounds are provided as non-toxic pharmaceutically acceptable salts as noted previously.

Compounds I and II may be administered by any suitable method, such as oral, parenteral (for example, intramuscular, intraperitoneal, intravenous, ICV, intracisternal injection or infusion, subcutaneous injection, or implant), inhalation spray, nasal, vaginal, rectal, sublingual, urethral (for example, urethral suppository) or topical routes of administration (for example, gel, ointment, cream, aerosol, etc.). Compounds I and II may be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds described herein can be used for treating humans.

The pharmaceutical compositions for the administration of compounds I and II may conveniently be presented in dosage unit form and may be prepared by any of the methods well known in the art of pharmacy. The pharmaceutical compositions can be, for example, prepared by uniformly and intimately bringing the active ingredient into association with a liquid carrier or a finely divided solid carrier or both, and then, if necessary, shaping the product into the desired formulation and/or placing it in appropriate packaging. In topical formulations of the disclosed compounds, the formulation is placed in an appropriate container (such as a squeeze-tube with a cap for dispensing ointments and creams). Alternatively, the dispenser may include a device for dispensing unit dosages of the drug (such as a bottle or dropper that dispenses a controlled pre-determined dosage of the drug to a target area). In the pharmaceutical composition the active object compound is included in an amount sufficient to produce the desired therapeutic effect. For example, pharmaceutical compositions described herein may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) or prodrug(s) may be formulated as solutions, gels, ointments, creams, suspensions, etc. as are well-known in the art. In addition to being suitable for administration to the skin, the solutions, gels, ointments, creams and suspensions are also well-suited for administration directly to the eye. One embodiment is a pharmaceutical formulation comprising compound I and/or compound II, where the formulation is selected from a solution, a gel, an ointment, a cream and a suspension. In one aspect, such formulations formulated for topical administration include a therapeutically effective amount of a compound I and/or compound II or a pharmaceutically acceptable salt thereof, such as a hydrochloride salt or a besylate salt in the case of compound I and, by way of example, a lysine, choline or arginine salt of compound II. Particular embodiments of formulations for use in the methods described herein include a therapeutically effective amount of the compound, a topical base, an antioxidant, an emollient, and an emulsifier. A person of skill in the art will appreciate that a therapeutically effective amount of the compound may vary, but typically a concentration ranging from 0.1% to 10% (w/w) will provide a therapeutically effective amount of the compound to the subject.

The topical base may comprise polyethylene glycol having a selected molecular weight. Particular embodiments comprise a polyethylene glycol having a molecular weight of from 3000 to 8000 Daltons as a topical base.

In certain embodiments, the formulation is an ointment, and may further include a water-miscible solvent, such as a polyalkylene glycol having an average molecular weight of from 200 Daltons to 600 Daltons. In certain embodiments the water-miscible solvent comprises PEG-400, and even more particularly PEG-400 substantially free of impurities. In certain embodiments, PEG-400 substantially free of impurities comprises less than 65 ppm formaldehyde, less than 10 ppm formaldehyde, or 1 ppm or less formaldehyde.

Topical formulations for use as described herein also can include a penetration enhancer, such as dimethyl isosorbide, propylene glycol, or combinations thereof; an emollient, such as water; a surfactant, such as sorbitan monostearate, a polyethylene glycol monostearate, D-α-tocopheryl polyethylene glycol 1000 succinate, a composition comprising glycol stearate/PEG32 stearate/PEG6 stearate, and combinations of surfactants; an antioxidant, such as butylated hydroxyanisole, butylated hydroxytoluene, ascorbic acid, α-tocopherol, and combinations thereof, with particular embodiments comprising butylated hydroxytoluene as an antioxidant; and an optional colorant, such as 0.05% to 0.25% (w/w) caramel colorant.

For particular embodiments, a concentration ranging from 0.1% to 10% (w/w) provides a therapeutically effective amount of the compound to the subject, and the pharmaceutical formulation further comprises: from 15% to 40% (w/w) of a topical base, such as a polyalkylene glycol with an average molecular weight of from 4000 to 5000 Daltons; from 25% to 50% (w/w) of a water-miscible solvent, such as a polyalkylene glycol with an average molecular weight of from 300 to 500 Daltons; from 10% to 20% (w/w) of a penetration enhancer, such as dimethyl isosorbide; from 3% to 15% (w/w) of an emollient, such as water; from 3% to 9% (w/w) of a surfactant, such as polyethylene glycol monostearate; and from 0.5% to 1.5% (w/w) butylated hydroxytoluene as an antioxidant.

Another embodiment of the pharmaceutical formulation comprises from 0.2% to 6% (w/w) of compound I or a pharmaceutically acceptable salt thereof; 30% to 40% (w/w) polyethylene glycol with an average molecular weight of from 4000 to 5000 Daltons; from 30% to 40% (w/w) polyethylene glycol with an average molecular weight of from 300 to 500 Daltons; 15% (w/w) dimethyl isosorbide; 3 to 5% (w/w) water; 5% (w/w) polyethylene glycol monostearate; 1% (w/w) butylated hydroxytoluene; and 0.05% caramel.

Yet another embodiment of the pharmaceutical formulation comprises 1% (w/w) compound I; 25% to 40% (w/w) polyethylene glycol with an average molecular weight of 4500 Daltons; and 30% to 45% (w/w) polyethylene glycol with an average molecular weight of 400 Daltons.

Yet another embodiment of the pharmaceutical formulation comprises 3% (w/w) compound I; 32% (w/w) polyethylene glycol with an average molecular weight of 4500 Daltons; and 38% to 42% (w/w) polyethylene glycol with an average molecular weight of 400 Daltons.

Yet another embodiment of the pharmaceutical formulation comprises 6% (w/w) compound I; 35% (w/w) polyethylene glycol with an average molecular weight of 4500 Daltons; and 33% to 35% (w/w) polyethylene glycol with an average molecular weight of 400 Daltons.

In one embodiment, the formulation is a solution. In another embodiment, the formulation is a gel. In another embodiment, the formulation is a suspension. In yet another embodiment, the formulation is a cream or ointment. One embodiment is any of the aforementioned formulations in a kit for topical or local administration. In one embodiment, the formulation is a liquid, for example a homogeneous liquid or a suspension, sold in a bottle which dispenses the formulation as drops or a liquid film (for example from an applicator tip that contacts a target area of the skin to dispense the liquid substantially only on a target area of the skin to be treated). In one embodiment, the formulation is a cream or ointment, sold in a tube which dispenses the formulation to a target area of the skin. In another embodiment, the compound is provided in a viscous liquid (such as carboxylmethylcellulose, hydroxypropylmethycellulose, polyethylene glycol, glycerin, polyvinyl alcohol, or oil containing drops) for rubbing into the skin or instilling in the eye. The formulations may have preservatives or be preservative-free (for example in a single-use container).

Compounds I and II can be used for manufacturing a composition or medicament, including medicaments suitable for topical administration, such as creams, ointments, jellies, gels, solutions or suspensions, etc. In certain embodiments, compounds I and II may be formulated for topical administration with polyethylene glycol (PEG). These formulations may optionally comprise additional pharmaceutically acceptable ingredients such as diluents, stabilizers and/or adjuvants. In particular embodiments, the topical formulations are formulated for the treatment of vitiligo.

Systemic formulations include those designed for administration by injection, for example, subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent or activating agents for activating the prodrug. The formulations for injection may be presented in unit dosage form, for example, in ampules or in multidose containers, and may contain added preservatives. They may also be provided in syringes, for example syringes with needles from injection of the drug into the skin, for example directly into a depigmented area of skin.

Alternatively, the injectable formulation may be provided in powder form for reconstitution with a suitable vehicle, including but not limited to sterile pyrogen free water, buffer, dextrose solution, etc., before use. The powder can include an activating agent for a prodrug, which activates the prodrug when the powder is solubilized in a vehicle. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art, and include dimethyl sulfoxide (DMSO) and dimethyl isosorbide. However, the penetrants can also be used to improve delivery of the active agents into the skin.

For oral administration, the pharmaceutical compositions may take the form of, for example, lozenges, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulfate). The tablets may be coated by methods well known in the art with, for example, sugars, films or enteric coatings. Additionally, the pharmaceutical compositions containing the 2,4-substituted pyrimidinediamine as active ingredient or prodrug thereof in a form suitable for oral use, may also include, for example, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient (including prodrug) in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents (for example, corn starch, or alginic acid); binding agents (for example starch, gelatin or acacia); and lubricating agents (for example magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. The pharmaceutical compositions described herein may also be in the form of oil-in-water emulsions.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol, Cremophore® or fractionated vegetable oils); and preservatives (for example, methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

The active compound(s) or prodrug(s) can be conveniently delivered in the form of an aerosol spray from pressurized packs or a nebulizer with the use of a suitable propellant, for example, dichlorodifluoromethane, trichlorofluoromethane, dichlorotetrafluoroethane, fluorocarbons, carbon dioxide or other suitable gas. When administering a pro-drug, it can be co-delivered and mixed thereby with an activating agent, for example to active compound II to compound I. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. Compounds I and II may also be administered in the form of suppositories for rectal or urethral administration of the drug. In particular embodiments, the compounds may be formulated as urethral suppositories, for example, for use in the treatment of fertility conditions, particularly in males, for example, for the treatment of testicular dysfunction.

According to the invention, 2,4-substituted pyrimidinediamine compounds can be used for manufacturing a composition or medicament, including medicaments suitable for rectal or urethral administration. The invention also relates to methods for manufacturing compositions including 2,4-substituted pyrimidinediamine compounds in a form that is suitable for urethral or rectal administration, including suppositories.

Included among the devices which may be used to administer particular examples of compounds I and II are those well-known in the art, such as, metered dose inhalers, liquid nebulizers, dry powder inhalers, sprayers, foamers, thermal vaporizers, and the like. Other suitable technology for administration of particular 2,4-substituted pyrimidinediamine compounds includes electrohydrodynamic aerosolizers. Sprays, aerosols, sponge-tipped applicators and foam dispensers can be used to administer the compounds, either per se or in formulations, directly to the skin, or by intradermal injection directly into depigmented patches caused by vitiligo.

Typically formulations for skin administration contain a pharmaceutically effective amount of a 2,4-pyrimidinediamine compound disclosed herein, such as from about 0.0001% to about 10% or more by weight (w/w). In certain formulations, the pharmaceutically effective amount of the compound is 0.0003% to about 0.1% (w/w), such as from about 0.003% to about 0.5% (w/w), from about 0.01% to about 0.03% (w/w), or from about 0.1% to about 10% (w/w). In other examples, the compound is present in at least 2%, 3% or 5% (w/w).

In certain examples an ophthalmic composition containing a presently disclosed 2,4-pyrimidinediamine compound for ocular administration (e.g., for vitiligo of the eye) includes a tonicity agent, a buffer, or both. In certain examples of ophthalmic compositions the tonicity agent is a simple carbohydrate or a sugar alcohol. As is known to one of ordinary skill in the art, tonicity agents may be used in the present compositions to adjust the tonicity of the composition, preferably to that of normal tears. Examples of suitable tonicity agents include, without limitation sodium chloride, potassium chloride, magnesium chloride, calcium chloride, carbohydrates, such as dextrose, fructose, galactose, polyols, such as sugar alcohols, including by way of example, mannitol, sorbitol, xylitol, lactitol, isomalt, maltitol and combinations thereof. Compositions containing a buffer contain, in some examples, a phosphate, citrate, or both.

The 2,4-substituted pyrimidinediamine compound(s) or prodrug(s) described herein, or compositions thereof, will generally be used in an amount effective to treat or prevent vitiligo. The compound(s) may be administered therapeutically to achieve therapeutic benefit or prophylactically to achieve prophylactic benefit. By therapeutic benefit is meant eradication or amelioration of vitiligo and/or eradication or amelioration of one or more of the symptoms associated with vitiligo such that the patient reports an improvement in feeling or condition, notwithstanding that the patient may still be afflicted with vitiligo. For example, administration of a compound to a patient suffering from vitiligo provides therapeutic benefit not only when the underlying depigmented patch is eradicated or ameliorated, but also when halting or slowing the progression of the disease, regardless of whether improvement in symptoms is realized.

For prophylactic administration, the compound may be administered to a patient at risk of developing vitiligo, such as those with a family history of vitiligo or premature graying of the hair. Other risk factors can be identified by those of skill in the art and may include Addison's disease, hypothyroidism, hyperthyroidism, alopecia areata, pernicious anemia, psoriasis, or adult-onset diabetes. Alternatively, prophylactic administration may be applied to avoid the progression of symptoms in a patient diagnosed with vitiligo.

The amount of compound administered will depend upon a variety of factors, including, for example, the particular type of vitiligo being treated, the mode of administration, the severity of the vitiligo, the age and weight of the patient, the bioavailability of the particular active compound, etc. Determination of an effective dosage is well within the capabilities of those skilled in the art. A skilled practitioner will be able to determine the optimal dose for a particular individual. Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro assays described in Examples 2 and 3 herein. Similarly, an initial dosage of prodrug for systemic use in animals may be formulated to achieve a circulating blood or serum concentration of the metabolite active compound that is at or above an $IC_{50}$ of the particular compound in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pergamon Press, and the references cited therein.

Initial dosages can also be estimated from in vivo data, using animal models such as those disclosed in Example 7. Animal models useful for testing the efficacy of compounds to treat or prevent the various diseases described above are well-known in the art. Dosage amounts for systemic administration will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Systemic dosage amount and interval may be adjusted individually to provide plasma levels of the compound(s) which are sufficient to maintain therapeutic or prophylactic effect. For example, the compounds may be administered once per week, several times per week (for example, every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation. In view of the much higher therapeutic index of topical administration to the skin, dosages can be increased beyond general systemic dosages without significant additional concern for side-effects and toxicities.

The foregoing disclosure pertaining to the dosage requirements for the 2,4-substituted pyrimidinediamine compounds is pertinent to dosages required for prodrugs, with the realization, apparent to the skilled artisan, that the amount of prodrug(s) administered will also depend upon a variety of factors, including, for example, the bioavailability of the particular prodrug(s), the conversion rate and efficiency into active drug compound under the selected route of administration, co-administration of an activating agent, etc. Determination of an effective dosage of prodrug(s) for a particular use and mode of administration is well within the capabilities of those skilled in the art.

For topical or ocular administration, effective dosages may be those where no significant systemic circulation of the compounds results from administration to the skin or eye, for example, where a topical formulation is applied directly to a depigmented patch and a very localized dose is utilized prior to significant systemic circulation.

IV. Methods

Disclosed herein are 2,4-substituted pyrimidinediamine compounds I and II, prodrugs, solvates, salts, N-oxides and pharmaceutical compositions thereof, for use in treating and/or preventing vitiligo. In particular, compounds I and/or II, are administered alone or in combination with other agents. In some examples, compositions comprising compound II may include activating agents to activate the prodrug compound II to compound I.

Compounds I and II (at least as a source of compound I) are potent, and thus can be administered locally (for example topically or by injection to the skin or mucous membrane) at very low doses, thus minimizing systemic adverse effects.

Compounds I and II are potent and selective inhibitors of JAK kinases and in particular JAK1/3-dependent cytokine signaling operative in T- and B-cells and Syk-dependent signaling in macrophages, dendritic cells, and B-cells. For example, Compound I has a half maximal effective concentration (EC50) in human cell-based assays against JAK3 and Syk in the range of 0.18 µM and 0.14 µM (Deuse et al. *Transplantation* 85(6) 885-892), respectively, and has little or no activity on other cytokine (IL-1β and TNFα) or receptor tyrosine kinase (RTK) signaling, and is not a broad inhibitor of cell proliferation.

Compound I is particularly selective for cytokine signaling pathways containing JAK3. As a consequence of this activity, the compounds may be used in a variety of in vitro, in vivo and ex vivo contexts to regulate or inhibit JAK kinase activity, signaling cascades in which JAK kinases play a role, and the biological responses effected by such signaling cascades. For example, in one embodiment, the compounds may be used to inhibit JAK kinase, either in vitro or in vivo, in virtually any cell type expressing the JAK kinase (such as hematopoietic cells). They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15 and IL-21 receptor signaling cascades. The compounds may also be used in vitro or in vivo to regulate, and in particular inhibit, cellular or biological responses affected by such JAK-dependent signal transduction cascades. Such cellular or biological responses include, but are not limited to, IL-4/ramos CD23 upregulation, IL-2 mediated T-cell proliferation, etc. Importantly, the compounds may be used to inhibit JAK kinases in vivo as a therapeutic approach towards the treatment or prevention of diseases mediated, either wholly or in part, by a JAK kinase activity. Such diseases are referred to as "JAK kinase mediated diseases."

Compounds I and II are inhibitors of Syk kinases. As a consequence, the compounds may be used in a variety of in vitro, in vivo and ex vivo contexts to regulate or inhibit Syk kinase activity, signaling cascades in which Syk kinases play a role, and the biological responses effected by such signaling cascades. For example, in one embodiment, the compounds may be used to inhibit Syk kinase, either in vitro or in vivo, in virtually any cell type expressing the Syk kinase.

While not wishing to be bound by theory, it is believed that compounds described herein are effective treatments of vitiligo due, at least in part, to their JAK and/or Syk inhibitory activity. In one embodiment, compound I and/or II are employed as salt forms. In a particular embodiment, compound II is used as a salt form. In one embodiment, the salt of compound II is selected from the sodium salt, the potassium salt, the calcium salt, the arginine salt and the choline salt.

Co-Administration

When used to treat vitiligo patches of the skin and/or mucous membranes, compounds I and II may be administered singly, as mixtures and/or in combination with other agents useful for activating a prodrug or treating diseases and/or disorders of the skin. Compounds I and/or II may be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, rituxan, PD4 inhibitors, p38 inhibitors, PDE4 inhibitors, and antihistamines, to name a few. Compounds I and II may be administered per se, in the form of prodrugs, salts, solvates, or N-oxides, or as pharmaceutical compositions, comprising the active compound and/or prodrug.

The pharmaceutical compositions disclosed herein can be co-administered (concurrently or sequentially) with a variety of other treatments applied to the skin, for example antibacterials (such as Bactroban® or Cleocin®); antipsoriasis medications (such as Micanol®); antifungal agents (such as Lamisil®, Lotrimin®, and Nizoral®); acne treatments (such as benzoyl peroxide topical preparations); treatments for seborrheic dermatitis (such as coal tar); corticosteroids; retinoids (such as Retin-A and Tazorac®) which are gels or creams derived from vitamin A that are used to treat conditions including acne; and wart treatments (such as salicylic acid), topical immunomodulators (such as tacrolimus or pimecrolimus), or psoralen (a UV sensitizer used in conjunction with phototherapy). Any of these agents can be provided in topical or cosmetic formulations, for example in lotions, ointments, creams, gels, soaps, shampoos, or adherent applicators such as patches.

The pharmaceutical compositions disclosed herein can also be co-administered (concurrently or sequentially) with a variety of other treatments that are not applied to the skin, for example treatments that are administered systemically, such as orally or parenterally. Examples of such systemic treatments include corticosteroids (such as Prednisone), antibiotics (such as erythromycin, tetracycline, and dicloxacillin), antifungal agents (such as ketoconazole and Diflucan®), antiviral agents (such as Valtrex®, acyclovir, and Famvir), corticosteroids, immunosuppressants (such as Cytoxan®, azathioprine, methotrexate, mycophenolate), biologics (such as Rituxan®, Enbrel®, Humira®, Remicade®, Stelara®, and Amevive®), and/or thyroid hormone replacement.

Other therapies that can be used in combination with compounds I and/or II include, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil, azathioprine, various antibodies, for example, antilymphocyte globulin (ALG), antithymocyte globulin (ATG), monoclonal anti-T-cell antibodies (OKT3), and irradiation. These various agents can be used in accordance with their standard or common dosages, as specified in the prescribing information accompanying commercially available forms of the drugs (see also, the prescribing information in the 2006 Edition of *The Physician's Desk Reference*). Azathioprine is currently available from Salix Pharmaceuticals, Inc. under the brand name Azasan®; mercaptopurine is currently available from Gate Pharmaceuticals, Inc. under the brand name Purinethol®; prednisone and prednisolone are currently available from Roxane Laboratories, Inc.; methyl prednisolone is currently available from Pfizer; sirolimus (rapamycin) is currently available from Wyeth-Ayerst under the brand name Rapamune®; tacrolimus is currently available from Fujisawa under the brand name Prograf®; cyclosporine is current available from Novartis under the brand name Sandimmune® and Abbott under the brand name Gengraf®; IMPDH inhibitors such as mycophenolate mofetil and mycophenolic acid are currently available from Roche under the brand name Cellcept® and Novartis under the brand name Myfortic®; azathioprine is currently available from Glaxo Smith Kline under the brand name Imuran®; and antibodies are currently available from Ortho Biotech under the brand name Orthoclone®, Novartis under the brand name Simulect® (basiliximab) and Roche under the brand name Zenapax® (daclizumab).

In one embodiment, the compound of formula I and/or II, or the pharmaceutically acceptable salt form thereof, is administered either in combination or adjunctively with systemic phototherapy (e.g., narrow-band UV-B phototherapy, 310-315 nm), psoralen photochemotherapy (PUVA: psoralens (e.g., 5-methoxypsoralen, 8-methoxypsoralen (0.1-0.3%), trimethylpsoralen) combined with UV-A light), excimer laser (308 nm) therapy. In some examples, topical tacrolimus (0.03-0.1%) ointment is combined with excimer laser therapy. Pimecrolimus (1%) cream may be combined with narrow-band UV-B treatment for vitiligo of the face. Vitamin D analogs (e.g., calcipotriol, tacalcitol) may be combined with narrow-band UV-B or PUVA treatment.

In another embodiment, compound I and/or compound II is administered either in combination or adjunctively with the therapies above and/or with a therapy for another disease. For example, the compound may be combined with thyroid hormone replacement therapy or with anti-inflammatory or immunomodulatory therapies.

In one embodiment, compound I and/or compound II is administered either in combination or adjunctively with an ophthalmic formulation of a drug such as an antihistamine, an antibiotic, an anti-inflammatory, an antiviral or a glaucoma medication for treating cases of vitiligo that primarily affect the eye or skin around the eye (such as the eyelids), and may be administered to or around the eye, for example in drops or ointments. When preparing these combination formulations, compound I and/or compound II may be combined with ophthalmic antibiotics (such as sulfacetamide, erythromycin, gentamicin, tobramycin, ciprofloxacin or ofloxacin); ophthalmic corticosteroids (such as prednisolone, fluorometholone or dexamethasone; ophthalmic non-steroidal anti-inflammatories (such as ibuprofen, diclofenac, ketorolac or flurbiprofen); ophthalmic antihistamines (such as livostin, patanol, cromolyn, alomide, or pheniramine); ophthalmic antiviral eye medications (such as triflurthymidine, adenine, arabinoside or idoxuridine); ophthalmic glaucoma medications (for example beta-blockers such as timolol, metipranolol, carteolol, betaxolol or levobunolol); ophthalmic prostaglandin analogues (such as latanoprost); ophthalmic cholinergic agonists (such as pilocarpine or carbachol); ophthalmic alpha agonists such as bromonidine or iopidine; ophthalmic carbonic anhydrase inhibitors (such as dorzolamide); and ophthalmic adenergic agonists (such as epinephrine or dipivefrin).

Additional compounds that can be substituted for compounds I and II in the disclosed methods are specifically contemplated herein and are described in Argade et al. U.S. Pat. No. 7,491,732, issued Feb. 17, 2009 and U.S. Patent Application Publication No. 2007/0203161, published Aug. 30, 2007, both of which are incorporated herein by reference.

V. Examples

Example 1

Compound Synthesis

Compounds I and II, as well as salts III-VII, are synthesized as described below or by analogy to the syntheses described below. Alternative syntheses would be appreciated by one of ordinary skill in the art.

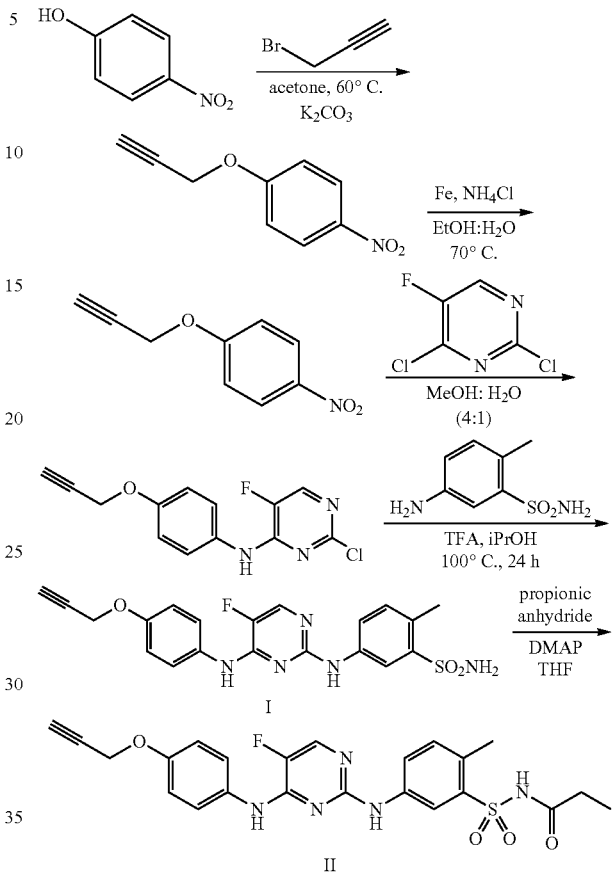

I: N2-(3-Aminosulfonyl-4-methylphenyl)-5-fluoro-N4-[4-(prop-2-ynyloxy)phenyl]-2,4-pyrimidinediamine 4-Nitrophenol (1.00 g, 7.19 mmol), propargyl bromide (80 wt % in toluene; 0.788 mL, 7.09 mmol), and K$_2$CO$_3$ (1.08 g, 7.84 mmol) were combined and stirred in acetone (16.0 mL) at 60° C. for 18 h. The reaction mixture was cooled to room temperature and diluted with water (200 mL). 4-(prop-2-ynyloxy)nitrobenzene was isolated as a white solid by suction filtration (1.12 g). $^1$H NMR (CDCl$_3$): δ 8.22 (d, J=9.0 Hz, 2H), 7.05 (d, J=9.0 Hz, 2H), 4.80 (d, J=2.4 Hz, 2H), 2.59 (t, J=2.4 Hz, 1H).

4-(Prop-2-ynyloxy)nitrobenzene (0.910 g, 5.13 mmol), iron (1.42 g, 25.3 mmol), and NH$_4$Cl (0.719 g, 12.8 mmol) were vigorously stirred in EtOH/water (1:1, 55 mL) at 70° C. for 15 minutes. The reaction mixture was filtered hot through diatomaceous earth and concentrated in vacuo. The residue was suspended in 10% 2N ammoniacal methanol in dichloromethane, sonicated, and filtered through diatomaceous earth. Concentration gave 4-(prop-2-ynyloxy)aniline as an oil which was used without further purification. $^1$H NMR (CDCl$_3$): δ 6.82 (d, J=8.7 Hz, 2H), 6.64 (d, J=8.7 Hz, 2H), 4.61 (d, J=2.4 Hz, 2H), 2.50 (t, J=2.4 Hz, 1H).

4-(prop-2-ynyloxy)aniline (0.750 g, 5.10 mmol) and 2,4-dichloro-5-fluoropyrimidine (1.27 g, 0.760 mmol, commercially available from Sigma-Aldrich of Milwaukee, Wis., USA) were stirred in MeOH/water (4:1, 35 mL) at room temperature for 18 h. The reaction mixture was diluted with EtOAc (200 mL) and washed with 1N HCl (50 mL) and brine (50 mL). The organic layer was dried (MgSO$_4$), filtered and concentrated in vacuo. The residue was purified by column chromatography (silica gel, hexanes ramped to EtOAc:hexanes (1:10)) to provide 2-chloro-5-fluoro-N4-[4-(prop-2-ynyloxy)phenyl]-4-pyrimidineamine as a light brown solid (0.514 g). $^1$H NMR (CDCl$_3$): δ 8.03 (d, J=2.7 Hz, 1H), 7.53 (d, J=8.7 Hz, 2H), 7.02 (d, J=8.7 Hz, 2H), 6.86 (s, 1H), 4.71 (d, J=2.4 Hz, 2H), 2.55 (t, J=2.4 Hz, 1H); LCMS: purity: 99%; MS (m/e): 279 (MH$^+$).

2-Chloro-5-fluoro-N4-[4-(prop-2-ynyloxy)phenyl]-4-pyrimidineamine (0.514 g, 1.85 mmol), 3-(aminosulfonyl)-4-methylaniline (0.689 g, 3.70 mmol, made by reduction of commercially available 2-methyl-5-nitrobenzenesulfonamide or synthesized as described below), and trifluoroacetic acid (0.186 mL, 2.41 mmol) were combined with iPrOH (6.0 mL) in a sealed vial and heated at 100° C. for 3 h. The reaction mixture was cooled to room temperature and diluted with 1N HCl (80 mL). N2-(3-Aminosulfonyl-4-methylphenyl)-5-fluoro-N4-[4-(prop-2-ynyloxy)phenyl]-2,4-pyrimidinediamine (I) was isolated as a white solid by suction filtration (0.703 g). $^1$H NMR (DMSO-d$_6$): δ 10.08 (bs, 2H), 8.19 (d, J=4.5 Hz, 1H), 7.89 (s, 1H), 7.74 (dd, J=2.4 and 8.4 Hz, 1H), 7.58 (d, J=8.7 Hz, 2H), 7.32 (bs, 2H), 7.23 (d, J=8.4 Hz, 1H), 6.97 (d, J=8.4 Hz, 2H), 4.79 (d, J=2.1 Hz, 2H), 3.59-3.55 (m, 1H), 2.53 (s, 3H); LCMS: purity: 97%; MS (m/e): 428 (MH$^+$).

II: 5-fluoro-N2-(4-methyl-3-propionylaminosulfonylphenyl)-N4-[4-(prop-2-ynyloxy)phenyl]-2,4-pyrimidinediamine N2-(3-Aminosulfonyl-4-methylphenyl)-5-fluoro-N4-[4-(prop-2-ynyloxy)phenyl]-2,4-pyrimidinediamine, I, (0.200 g, 0.467 mmol), DMAP (40 mg, 0.33 mmol)) and triethylamine (0.118 mL, 0.847 mmol) were stirred in THF (6.0 mL). Propionic anhydride (0.180 mL, 1.40 mmol) was added to the solution drop wise. The reaction mixture was stirred at room temperature overnight. The solution was diluted with ethyl acetate (50 mL) and washed with water (5×25 mL) and brine (10 mL). The organic layer was dried (MgSO$_4$), filtered, and evaporated. The residue was suspended in ethyl acetate (25 mL), sonicated and the solid collected by filtration to give 5-fluoro-N2-(4-methyl-3-propionylaminosulfonylphenyl)-N4-[4-(prop-2-ynyloxy)phenyl]-2,4-pyrimidinediamine, II, (0.20 g). $^1$H NMR (DMSO-d$_6$): δ 12.01 (s, 1H), 9.44 (s, 1H), 9.26 (s, 1H), 8.16 (d, J=2.4 Hz, 1H), 8.06 (dd, J=0.3 and 3.3 Hz, 1H), 8.00 (dd, J=2.1 and 7.8 Hz, 1H), 7.69 (d, J=8.7 Hz, 2H), 7.19 (d, J=8.4 Hz, 1H), 6.95 (d, J=8.7 Hz, 2H), 4.77 (d, J=2.1 Hz, 2H), 3.56 (t, J=2.1 Hz, 1H), 2.49 (s, 3H), 2.24 (q, J=7.2 Hz, 2H), 0.89 (t, J=7.2 Hz, 3H); LCMS: purity: 98%; MS (m/e): 484 (MH$^+$).

III: 5-fluoro-N2-(4-methyl-3-propionylaminosulfonylphenyl)-N4-[4-(prop-2-ynyloxy)phenyl]-2,4-pyrimidinediamine mono-sodium salt 5-Fluoro-N2-(4-methyl-3-propionylaminosulfonylphenyl)-N4-[4-(prop-2-ynyloxy)phenyl]-2,4-pyrimidinediamine, II, (0.125 g, 0.258 mmol) was suspended in acetonitrile (1.5 mL) and water (1.5 mL) and cooled in an ice bath. A solution of 1N NaOH aq. (0.260 mL) was added drop wise. The reaction mixture was stirred until it became clear, filtered through glass wool, and lyophilized to give the sodium salt of II. $^1$H NMR (DMSO-d$_6$): δ 9.17 (bs, 2H), 8.01 (d, J=3.6 Hz, 1H), 7.89 (s, 1H), 7.78-7.69 (m, 3H), 6.99-6.92 (m, 3H), 4.76 (d, J=2.1 Hz, 1H), 2.43 (s, 3H), 1.95 (q, J=7.2 Hz, 2H), 0.86 (t, J=7.2 Hz, 3H); LCMS: purity: 98%; MS (m/e): 484 (MH+).

The following compounds were made in a similar fashion to those above.

IV: 5-Fluoro-N2-[4-methyl-3-(N-propionylaminosulfonyl)phenyl]-N4-[4-(2-propynyloxy)phenyl]-2,4-pyrimidinediamine Potassium Salt $^1$H NMR (DMSO-d$_6$): δ 9.16 (s, 1H), 9.14 (s, 1H), 8.01 (d, J=3.6 Hz, 1H), 7.85 (d, J=2.1 Hz, 1H), 7.75-7.70 (m, 3H), 6.97-6.92 (m, 3H), 4.76 (d, J=1.8 Hz, 2H), 3.55 (t, J=2.4 Hz, 1H), 2.42 (s, 3H), 1.91 (q, J=7.5 Hz, 2H), 0.85 (t, J=7.5 Hz, 3H); LCMS: purity: 97%; MS (m/z): 484 (parent, MH$^+$).

V: 5-Fluoro-N2-[4-methyl-3-(N-propionylaminosulfonyl)phenyl]-N4-[4-(2-propynyloxyl)phenyl]-2,4-pyrimidinediamine Calcium Salt $^1$H NMR (DMSO-d$_6$): δ 9.16 (s, 2H), 8.00 (d, J=3.6 Hz, 1H), 7.88 (d, J=1.8 Hz, 1H), 7.75-7.69 (m, 3H), 6.97-6.92 (m, 3H), 4.76 (d, J=1.8 Hz, 2H), 3.55 (t, J=2.1 Hz, 1H), 2.43 (s, 3H), 1.94 (q, J=7.5 Hz, 2H), 0.87 (t, J=7.5 Hz, 3H); LCMS: purity: 98%; MS (m/z): 484 (parent, MH$^+$).

VI: 5-Fluoro-N2-[4-methyl-3-(N-propionylaminosulfonyl)phenyl]-N4-[4-(2-propynyloxy)phenyl]-2,4-pyrimidinediamine Arginine Salt $^1$H NMR (D$_2$O): δ 7.61 (d, J=3.9 Hz, 1H), 7.57-7.55 (m, 1H), 7.36-7.31 (m, 1H), 7.12 (d, J=8.7 Hz, 2H), 6.88 (d, J=8.7 Hz, 1H), 6.72 (d, J=9.0 Hz, 2H), 4.77-4.75 (m, 2H), 3.60 (t, J=6.0 Hz, 1H), 3.09 (t, J=6.9 Hz, 2H), 2.84-2.81 (m, 1H), 2.35 (s, 3H), 2.03 (q, J=5.7 Hz, 2H), 1.80-1.72 (m, 2H), 1.61-1.48 (m, 2H), 0.855 (t, J=7.5 Hz, 3H); LCMS: purity: 98%; MS (m/z): 484 (parent, MH$^+$).

VII: 5-Fluoro-N2-[4-methyl-3-(N-propionylaminosulfonyl)phenyl]-N4-[4-(2-propynyloxy)phenyl]-2,4-pyrimidinediamine Choline Salt $^1$H NMR (DMSO-d$_6$): δ 9.16 (s, 2H), 8.00 (d, J=3.6 Hz, 1H), 7.85 (d, J=1.8 Hz, 1H), 7.75-7.69 (m, 3H), 6.97-6.90 (m, 3H), 5.27 (t, J=4.8 Hz, 1H), 4.76 (d, J=1.8 Hz, 2H), 3.86-3.77 (m, 2H), 3.56-3.54 (m, 1H), 3.40-3.54 (m, 2H), 3.08 (s, 9H), 2.42 (s, 3H); LCMS: purity: 99%; MS (m/z): 484 (parent, MH$^+$).

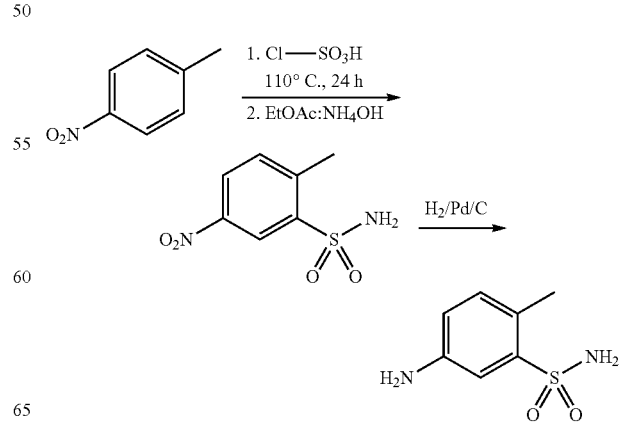

5-amino-2-methylbenzenesulfonamide 4-methylnitrobenzene (20 mmol) is treated at 0° C. with chlorosulfonic acid (5.29 mL, 80 mmol) and then, after bringing the homogeneous solution to room temperature, it was stirred at 110° C. for 24 hours. The resulting slurry was then poured over ice water (100 gm), extracted with diethyl ether (3×75 mL), and the organic phase washed with water (75 mL), then dried over anhydrous sodium sulfate. The solvent was then removed under reduced pressure to afford the crude sulfonyl chloride which was taken up in ethyl acetate and stirred with ammonium hydroxide overnight at room temperature. After the ethyl acetate layer was separated, the aqueous layer was extracted with ethyl acetate. The organic layers were combined, dried over anhydrous sodium sulfate and the solvent was removed under reduced pressure. The oil obtained was purified by column chromatography (silica gel, hexanes then 10%, 20%, up to 50% ethyl acetate in hexanes to afford 3-aminosulfonyl-4-methylnitrobenzene, LCMS: purity: 95%; MS (m/e): 217 (MH+).

To a solution of 3-aminosulfonyl-4-methylnitrobenzene in dichloromethane and methanol was added 10% Pd/C and the mixture shaken under a hydrogen atmosphere at 50 psi for 15 minutes. The mixture was filtered through diatomaceous earth and the filter cake was washed with methanol. The combined organic solvents were concentrated under reduced pressure to give crude product, which was further purified by flash column chromatography (ethyl acetate: hexanes 1:1) to give 3-aminosulfonyl-4-methylaniline, LCMS: purity: 87%; MS (m/e): 187 (MH+).

Example 2

Assay for Ramos B-Cell Line Stimulated with IL-4

One means of assaying for JAK inhibition is detection of the effect of compounds I and II on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (for example, the 2,4-substituted pyrimidinediamine compounds described herein) on the JAK1 and JAK3 kinases, human Ramos B cells are stimulated with human IL-4. Twenty to 24 hours post stimulation, cells are stained for upregulation of CD23 and analyzed using flow cytometry (FACS). A reduction of the amount of CD23 present compared to control conditions indicates the test compound actively inhibits the JAK kinase pathway. An exemplary assay of this type is described in greater detail below.

B-cells stimulated with cytokine Interleukin-4 (IL-4) activate the JAK/Stat pathway through phosphorylation of the JAK family kinases, JAK-1 and JAK-3, which in turn phosphorylate and activate the transcription factor Stat-6. One of the genes upregulated by activated Stat-6 is the low affinity IgE receptor, CD23. To study the effect of inhibitors on the JAK family kinases, human Ramos B cells are stimulated with human IL-4.

The Ramos B-cell line was acquired from ATCC (ATCC Catalog No. CRL-1596). The cells were cultured in RPMI 1640 (Cellgro, MediaTech, Inc., Herndon, Va., Cat No. 10-040-CM) with 10% fetal bovine serum (FBS), heat inactivated (JRH Biosciences, Inc, Lenexa, Kans., Cat No. 12106-500M) according to ATCC propagation protocol. Cells were maintained at a density of $3.5 \times 10^5$. The day before the experiment, Ramos B-cells were diluted to $3.5 \times 10^5$ cells/mL to ensure that they were in a logarithmic growth phase.

Cells were spun down and suspended in RPMI with 5% serum. $5 \times 10^4$ cells were used per point in a 96-well tissue culture plate. Cells were pre-incubated with compound or DMSO (Sigma-Aldrich, St. Louis, Mo., Cat No. D2650) vehicle control for 1 hour in a 37° C. incubator. Cells were then stimulated with IL-4 (Peprotech Inc., Rocky Hill, N.J., Cat No. 200-04) for a final concentration of 50 units/mL for 20-24 hours. Cells were then spun down and stained with anti-CD23-PE (BD Pharmingen, San Diego, Calif., Cat No. 555711) and analyzed by FACS. Detection was performed using a BD LSR I System Flow Cytometer, purchased from Becton Dickinson Biosciences of San Jose, Calif. The $IC_{50}$ calculated based on the results of this assay are provided in Table 1.

Example 3

Primary Human T-Cell Proliferation Assay Stimulated with IL-2

The JAK activity of the compounds described herein may further be characterized by assaying the effect of compounds I and II described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with compounds I and II in the presence of IL-2 for 72 hours and at the assay endpoint intracellular ATP concentrations are measured to assess cell viability. A reduction in cell proliferation compared to control conditions is indicative of inhibition of the JAK kinase pathway. An exemplary assay of this type is described in greater detail below.

Primary human T-cells derived from peripheral blood and pre-activated through stimulation of the T-cell receptor and CD28, proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum:ficoll interface were recovered and washed twice with 5 volumes of PBS. The cells were resuspended in Yssel's medium (Gemini Bio-products, Woodland, Calif., Catalog #400-103) containing 40 U/mL recombinant IL2 (R and D Systems, Minneapolis, Minn., Catalog #202-IL (20 µg)) and seeded into a flask pre-coated with 1 µg/mL anti-CD3 (BD Pharmingen, San Diego, Calif., Catalog #555336) and 5 µg/mL anti-CD28 (Immunotech, Beckman Coulter of Brea Calif., Catalog #IM1376). The primary T-cells were stimulated for 3-4 days, then transferred to a fresh flask and maintained in RPMI with 10% FBS and 40 U/mL IL-2.

Primary T-cells were washed twice with PBS to remove the IL-2 and resuspended in Yssel's medium at $2 \times 10^6$ cells/mL. 50 µL of cell suspension containing 80 U/mL IL-2 was added to each well of a flat bottom 96 well black plate. For the unstimulated control, IL-2 was omitted from the last column on the plate. Compounds were serially diluted in dimethyl sulfoxide (DMSO, 99.7% pure, cell culture tested, Sigma-Aldrich, St. Louis, Mo., Catalog No. D2650) from 5 mM in 3-fold dilutions, and then diluted 1:250 in Yssel's medium. 50 µL of 2× compound was added per well in duplicate and the cells were allowed to proliferate for 72 hours at 37° C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to room temperature. After mixing the Cell Titer-Glo reagent and diluent together, 100 µL was added to each well. The plates were mixed on an orbital shaker for two minutes to induce lysis and incubated at room temperature for an additional ten minutes to allow the signal to equilibrate. Detection was performed using a Wallac Victor2 1420 multilabel counter purchased from Perkin Elmer, Shelton, Conn. The $IC_{50}$ calculated based on the results of this assay are provided in Table 1.

Example 4

A549 Epithelial Line Stimulated with IFNγ

The JAK activity of the compounds described herein may also be characterized by assaying the effect of compounds I and II described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated. Exemplary assays of this type are described in greater detail below and in Example 6.

A549 lung epithelial cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The A549 lung epithelial carcinoma cell line originated from the American Type Culture Collection. Routine culturing was with F12K media (Mediatech Inc., Lenexa, Kans., Cat. No. 10-025-CV) with 10% fetal bovine serum, 100 I.U. penicillin and 100 ng/mL streptomycin (complete F12k media). Cells were incubated in a humidified atmosphere of 5% $CO_2$ at 37° C. Prior to use in the assay, A549 cells were washed with PBS and trypsinized (Mediatech Inc., Cat. No. 25-052-CI) to lift the cells. The trypsin cell suspension was neutralized with complete F12K media and centrifuged to pellet the cells. The cell pellet was resuspended in complete F12K media at a concentration of $2.0×10^5$/mL. Cells were seeded at 20,000 per well, 100 µL total volume, in a flat bottom tissue culture plate and allowed to adhere overnight.

On day two, A549 cells were pre-incubated with a 2,4-substituted pyrimidinediamine test compound or DMSO (control) (Sigma-Aldrich, St. Louis, Mo., Catalog No. D2650) for 1 hour. The cells were then stimulated with IFNγ (75 ng/mL) (Peprotech Inc., Rocky Hill, N.J., Cat. No. 300-02) and allowed to incubate for 24 hours. The final test compound dose range was 30 µM to 14 nM in 200 µL F12K media containing 5% FBS, 0.3% DMSO.

On day three, the cell media was removed and the cells were washed with 200 µL PBS (phosphate buffered saline). Each well was trypsinized to dissociate the cells, then neutralized by addition of 200 µL complete F12K media. Cells were pelleted and stained with an APC conjugated mouse anti-human ICAM-1 (CD54) (BD Pharmingen, San Diego, Calif., Catalog #559771) antibody for 20 minutes at 4° C. Cells were washed with ice cold FACS buffer (PBS+ 2% FBS) and surface ICAM-1 expression was analyzed by flow cytometry. Detection was performed using a BD LSR I System Flow Cytometer, purchased from BD Biosciences of San Jose, Calif. Events were gated for live scatter and the geometric mean was calculated (Becton-Dickinson Cell-Quest software version 3.3, Franklin Lakes, N.J.). Geometric means were plotted against the compound concentration to generate a dose response curve. The $IC_{50}$ calculated based on the results of this assay are provided in Table 1.

Example 5

U937 IFNγICAM1 FACS Assay

U937 human monocytic cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The U937 human monocytic cell line was obtained from ATCC of Rockville Md., catalog number CRL-1593.2, and cultured in RPM1-1640 medium containing 10% (v/v) FCS. U937 cells were grown in 10% RPMI. The cells were then plated at a concentration of 100,000 cells per 160 µL in 96 well flat bottom plates. The test compounds were then diluted as follows: 10 mM test compound was diluted 1:5 in DMSO (3 µL 10 mM test compound in 12 µL DMSO), followed by a 1:3 serial dilution of test compound in DMSO (6 µL test compound serially diluted into 12 µL DMSO to give 3-fold dilutions). Then 4 µL of test compound was transferred to 76 µL of 10% RPMI resulting in a 10× solution (100 µM test compound, 5% DMSO). For control wells, 4 µL of DMSO was diluted into 76 µL 10% RPMI.

The assay was performed in duplicate with 8 points (8 3-fold dilution concentrations from 10 µl) and with 4 wells of DMSO only (control wells) under stimulated conditions and 4 wells of DMSO only under unstimulated conditions.

The diluted compound plate was mixed 2× using a multimek (Beckman Coulter of Brea, Calif.) and then 20 µL of the diluted compounds was transferred to the 96-well plate containing 160 µL of cells, which were then mixed again twice at low speeds. The cells and compounds were then pre-incubated for 30 minutes at 37° C. with 5% $CO_2$.

The 10× stimulation mix was made by preparing a 100 ng/mL solution of human IFNγ in 10% RPMI. The cells and compound were then stimulated with 20 µL of IFNγ stimulation mix to give a final concentration of 10 ng/mL IFNγ, 10 µM test compound, and 0.5% DMSO. The cells were kept under conditions for stimulation for 18-24 hours at 37° C. with 5% $CO_2$.

The cells were transferred to a 96 well round bottom plate for staining and then kept on ice for the duration of the staining procedure. Cells were spun down at 1000 rpm for 5 minutes at 4° C., following which the supernatant was removed. Following removal of the supernatant, 1 µL APC conjugated mouse anti-human ICAM-1 antibody was added per 100 µL FACS buffer. The cells were then incubated on ice in the dark for 30 minutes. Following incubation, 150 µL of FACS buffer was added and the cells were centrifuged at 1000 rpm for 5 minutes at 4° C., following which the supernatant was removed. After removal of the supernatant, 200 µL of FACS buffer was added and the cells were resuspended. After suspension, the cells were centrifuged at 1000 rpm for 5 min at 4° C. Supernatant was then removed prior to resuspension of the cells in 150 µL FACS buffer.

Detection was performed using a BD LSR I System Flow Cytometer, purchased from BD Biosciences of San Jose, Calif. The live cells were gated for live scatter and the geometric mean of ICAM-APC was measured (Becton-Dickinson CellQuest software version 3.3, Franklin Lakes, N.J.). Both % live cells and ICAM-1 expression was analyzed. The assays for the test compounds were carried out in parallel with a control compound of known activity. The $EC_{50}$ for the control compound is typically 40-100 nM. The $IC_{50}$ calculated based on the results of this assay are provided in Table 1.

TABLE 1

| Compound | Example 2 | Example 3 | Example 4 | Example 5 |
|----------|-----------|-----------|-----------|-----------|
| I        | 0.056     | 0.181     | 11.338    | 0.565     |
| II       | 9.655     |           |           |           |
| III      | 3.972     |           |           |           |
| IV       | 2.318     | 5.560     |           |           |
| V        | 0.373     |           |           | 25.126    |
| VI       | 0.104     | 0.262     | 4.973     | 0.424     |
| VII      | 0.022     | 0.053     |           | 0.140     |

Example 6

Pharmaceutical Formulations

This example describes pharmaceutical formulations containing compound I or II (which will be understood to also include salts thereof). Such formulations are prepared as known to those of skill in the art and additional formulations will be readily apparent to those of skill in the art upon consideration of this Example and additional disclosure herein.

Each of the above formulations, 1-7, are prepared with compound I or II in three dosage concentrations: 0.001%, 0.003% and 0.01% (w/w). Each formulation is prepared by adding the specified amount of a tonicity agent (mannitol) to a flask, heating to about 50° C. in about half the final volume of the specified buffer (phosphate or citrate). After heating, the appropriate amount of compound I or II is added along with the additional excipients (glycerin and/or PEG400) as indicated. Purified water is added in sufficient quantity. The mixture is stirred to homogeneity (about five minutes) and then filtered through a sterilizing filter membrane into a sterile vessel. If necessary, pH is adjusted by addition of 1.0 N NaOH.

Optionally, formulations having a higher concentration of compound I or II (for example, 0.03% w/w) can include a surfactant and optionally a stabilizing polymer. With reference to formulations 6 and 7, preferred surfactants include Triton® X114 and tyloxapol, which are commercially available from Sigma-Aldrich (of St. Louis, Mo.) and Pressure Chemical Company (of Pittsburgh, Pa.), respectively. Preferred stabilizing polymers include the carbomer Carbopol® 974p (commercially available from Lubrizol, of Wickliffe, Ohio).

Formulations 6 and 7 are prepared by dispersing the carbomer first in the surfactant containing buffer at 10× of their final concentration (e.g. 3% tyloxapol in 50 mM phosphate buffer at pH 6.5 with 2.5% mannitol and 5% Carbopol® 974p). Either compound I or compound II is then dispersed in this preconcentrate also at 10× of its final concentration. The mixture is homogenized, with final formulation being obtained by 10× dilution of filtered preconcentrate in a matching buffer.

Methods of formulating and testing the drugs for topical application are described, for example, in Remington, The Science and Practice of Pharmacy (21$^{st}$ edition), pages 872-882 (2006). The drug is formulated for delivery of drug to a desired depth of the skin surface, while avoiding unwanted systemic absorption of the drug. Various penetration enhancers can be added to the composition, such as an alcohol, alkyl methyl sulfoxide, pyrrolidone, laurocapram, dimethyl formamide, tetrahydrofurfuryl alcohol, an amphiphile, or other miscellaneous enhancers such as clofibric acid amide, hexamethylene lauramide, proteolytic enzymes, terpenes or sesquiterpenes. The penetration enhancers improve drug delivery into the skin.

In one specific example of the formulation, a 60:20:20 ethanol:propylene glycol:water system is used with sufficient propylene glycol to maintain 0.5-2% of the active compound.

TABLE 2

| Formulation No. | Formulation Components |
|-----------------|------------------------|
| 1 | 50 mM pH 7.4 phosphate buffer, 0.05% Tween® 80, 0.5% NaCl |
| 2 | 50 mM pH 7.4 phosphate buffer, 0.36% HPMC, 0.2% glycerin, 1% PEG400, 0.35% NaCl |
| 3 | 5 mM pH 7.4 phosphate buffer, 0.36% HPMC, 0.2% glycerin, 1% PEG400, 5% Cremophor® ELP, 4.3% mannitol |
| 4 | 10 mM pH 5.8 citrate buffer, 4.2% mannitol |
| 5 | 10 mM pH 5.8 citrate buffer, 4.2% mannitol, 0.36% HPMC, 0.2% glycerin |
| 6 | 0.3% tyloxapol, 0.5% Carbopol® 974P, 2.25% mannitol, 50 mM pH 6.5 phosphate buffer, 230 mOsm/kg |
| 7 | 0.3% tyloxapol, 0.1% Carbopol® 974P, 2.25% mannitol, 50 mM pH 6.5 phosphate buffer, 230 mOsm/kg |

Common ingredients which may be used to administer the compound in a topical formulation are vehicles, for example hydrophobic vehicles such as hydrocarbons, liquid petrolatum (mineral oil, liquid paraffin, paraffin oil), white petrolatum (petroleum jelly, Vaseline®), yellow petrolatum (petroleum jelly), squalane (perhydrosqualene, spinacane), and silicones; silicones such as liquid polydimethylsiloxanes (dimethicone, silastic, medical grade silicone oil), alcohols such as lauryl alcohols (1-dodecanol, dodecyl alcohols), myristyl alcohols (tetradecanol, tetradecyl alcohols), cetyl alcohols (hexadecanol, ethal, palmityl alcohols), stearyl alcohols (stenol, cetosteryl alcohols), oleyl alcohols (ocenol); sterols such as sterol esters; lanolin such as hydrous wool fat, lanum; anhydrous lanolin (such as wool fat, anhydrous lanum, agnin); semi synthetic lanolins; carboxylic acids such as lauric acid, myristic acid, palmitic acid, stearic acid, oleic acid; esters and polyesters, such as cholesterol esters (stearate), ethylene glycol monoesters, propylene glycol monoesters, glyceryl monoesters, glyceryl monostearate, sorbitol monoesters, sorbitan monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, isopropyl palmitate; ethers and polyethers such as polyethylene-polypropylene glycols (pluronics).

Water-miscible vehicles that may be used as co-solvents include polyols and polyglycols such as propylene glycol (1,2-propanediol), glycerin (glycerol), liquid polyethylene glycol, solid polyethylene glycol (hard macrogol, carbowax), 1,2-phenol-hexanetriol, sorbitol solution, esters and polyesters such as polyoxyethylene sorbitain monoesters (stearate-tweens) and polyoxy ethylene sorbitan polyesters (tweens); ethers and polyethers such as polyethylene glycol monocetyl ether (cetomacrogol 1000) and polyethylene-polypropylene glycols (pluronics).

Various structural matrix formers can be added to the composition, for example hydrocarbons such as white petrolatum (petroleum jelly, Vaseline®), yellow petrolatum (petroleum jelly), paraffin (paraffin wax, hard paraffin), microcrystalline wax, ceresin (mineral wax, purified ozokerite); silicones such as fumed silica (cab-O-sil), bentonite (colloidal aluminum silicate), and veegum (colloidal magnesium aluminum silicate); polyols and polyglocols such as solid polyethylene glycol (hard macrogol, carbowax); alcohols such as cetyl alcohols (hexadecanol, ethal, palmityl alcohols), stearyl alcohols (stenol, cetosteryl alcohols); sterold and sterol esters such as cholesterol (cholesterin), lanolin, anhydrous lanolin, and semisynthetic lanolin; carboxylic acids such as lauric acid, myristic acid, palmitic acid, stearic acid, oleic acid; and esters or polyesters such as bees wax, white bees wax (bleached bees wax), Carnauba wax, myricin, cholesterol esters (stearate), polyoxyethylene sorbitain, lard or hydrogenated oils.

The compositions may further include suspending, jelling or viscosity inducing agents, for example silicones such as fumed silica (cab-O-sil), bentonite (colloidal aluminium silicate), or veegum (colloidal magnesium aluminium silicate); polycarboxylates, polysulfates or polysaccharides such as agar, alginates, carragen, acacia, tragacanth, methylcellulose, carboxy methylcellulose, hydroxy ethyl cellulose, carboxy vinyl polymer, gelatin, pectin, xanthan, polyacrylic acid.

Some embodiments may include a water-in-oil emulsifier such as a sterol or sterol ester, for example cholesterol (cholesterin), lanolin (hydrous wool fat, lanum), anhydrous lanolin (wool fat, anhydrous lanum, agnin), or semi synthetic lanolin; carboxylic acids such as Na+, K+, ethanolamin salts of lauric acid, myristic acid, palmitic acid, stearic acid, oleic acid, or an ether or polyether such as polyethylene-polypropylene glycols (pluronics). If an oil-in-water (o/w) emulsifier is desired, examples are esters and polyesters such as polyoxyethylene sorbitain monoesters (stearate-tweens), polyoxy ethylene esters (stearate-polyethylene glycol monoesters, Myrj), polyoxy ethylene sorbitan polyesters (tweens); ethers and polyethers such as polyethylene glycol monocetyl ether (cetomacrogol 1000) or polyethylene-polypropylene glycols (pluronics), and others such as sodium lauryl sulfate, borax (sodium borate), ethanolamine, or triethanolamine.

Suitable surfactants for use in the formulations include, but are not limited to, nonionic surfactants like Surfactant 190 (dimethicone copolyol), polysorbate 20 (Tween® 20), polysorbate 40 (Tween® 40), polysorbate 60 (Tween® 60), polysorbate 80 (Tween® 80), lauramide DEA, cocamide DEA, and cocamide MEA, amphoteric surfactants like oleyl betaine and cocamidopropyl betaine (Velvetex® BK-35), and cationic surfactants like Phospholipid PTC (Cocamidopropyl phosphatidyl PG-dimonium chloride). Appropriate combinations or mixtures of such surfactants may also be used.

Suitable moisturizers for use in the formulations of the present invention include, but are not limited to, lactic acid and other hydroxy acids and their salts, glycerin, propylene glycol, butylene glycol, sodium PCA, Carbowax™ 200, Carbowax™ 400, and Carbowax™ 800. Suitable emollients for use in the formulations of the present invention include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl® 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol® 840 (manufactured by Huls; propylene glycol dicaprylate/dicaprate). In addition, appropriate combinations and mixtures of any of these moisturizing agents and emollients may be used in accordance with the present disclosure.

The composition may also include preservatives and antimicrobials, such as benzalkonium chloride, benzoic acid, benzyl alcohol, bronopol, chlorhexidine, chlorocresol, imidazolidinyl urea, paraben esters, phenol, phenoxyethanol, potassium sorbate, or sorbic acid; antioxidants such as α-tocopherol, ascorbic acid, ascorbyl palmitate, butylated hydroxyanisole, sodium ascorbate, sodium metabisulfite; chelating agents such as citric acid or edetic acid; buffers such as citric acid and salts, phosphoric acid and salts, $H_3PO_4/NaH_2PO_4$, glycine, acetic acid, triethanolamine, or boric acid; humectants such as glycerin (glycerol), propylene glycol (E 1520), glyceryl triacetate (E1518), sorbitol (E420), xylitol and malitol (E965), polydextrose (E1200), quillaia (E999), lactic acid, urea or lithium chloride; and/or a sequestering antioxidant such as citric acid and it salts ethylenediaminetetraacetic acid (Versene, EDTA).

A particular embodiment of the topical treatment may be an ointment, which is a semisolid preparation intended for external application to the skin or mucous membranes. In a specific example, the ointment is based on petrolatum. The ointment does not contain sufficient water to separate into a second phase at room temperature. A water-soluble ointment may be formulated with polyethylene glycol. Ointments are ideal emollients with good skin penetration and adherence to surfaces. The ointment is in a convenient container such as a tube or jars.

Alternatively, the topical dosage form is a cream in which the compounds are dissolved or suspended in water removable or emollient bases. The creams may be either water-in-oil or oil-in-water compositions. Immiscible compounds may be combined by mechanical agitation or heat using wet gum, dry gum, bottle, and beaker methods. In some embodiments, the cream is an oil-in-water emulsion or aqueous microcrystalline dispersion of long chain fatty acids or alcohols that are water washable and more cosmetically and aesthetically acceptable.

In other embodiments, the active ingredients are provided for administration in a paste, which can be considered an ointment into which a high percentage of insoluble solids have been added, for example as much as 50% by weight. The paste is much stiffer than the ointment due to the presence of solids, which form a particulate matrix over and above the ointment structure already present. Ingredients such as starch, zinc oxide, calcium carbonate, and talc are used as the solid phase. Pastes provide a particularly good protective barrier on skin. Like ointment, a paste forms an unbroken, relatively water impermeable film on the skin surface; unlike ointment the film is opaque and therefore an effective sun filter.

In yet other embodiments, the active agent is provided in a gel, jelly or lotion. Gels are semisolid systems consisting of dispersions of small or large molecules in an aqueous liquid vehicle rendering jelly-like through the addition of gelling agent. Among the gelling agents used are synthetic macromolecules such as carbomer 934, and cellulose derivatives such as carboxymethylcellulose or hydroxypropylmethyl-cellulose. Gels are compatible with many substances and may contain penetration enhancers to improve delivery into the skin. The gels may be either single phase gels in which the macromolecules are uniformly distributed throughout a liquid with no apparent boundaries between the dispersed macromolecules and the liquid, or double phase gels in which the gel mass consists of floccules of small distinct particles, often referred to as a magmas. A jelly contains a water-soluble base prepared from natural gums such as tragacanth, pectin, alginate, or boroglycerin, or from synthetic derivatives of a natural substance such as methylcellulose or carboxymethylcellulose. A lotion is a clear solution containing 25-50% alcohol, which optionally contains an antiseptic, or emollient. Other optional ingredients that may be added to the lotion are an extract of witchhazel, menthol, glycerin, boric acid, alum, or potassium oxyquinoline.

In another embodiment the compound is applied in a powder, which contains very fine particle sizes that produce large surface area per unit weight to covers a larger surface area of the body and provide light dispersion. Alternatively the compound is applied in a solution, which is a liquid preparations of soluble chemicals dissolved in solvents such as water, alcohol, or propylene glycol. In yet other examples, it is an emulsion, which is a two-phase preparation in which one phase (the dispersed or internal phase) is finely dispersed in the other (continuous or external phase). The dispersed phase can have either a hydrophobic-base (oil-in-water) or aqueous base (water-in-oil). Because there are two incompatible phases in close conjunction, the emulsion would typically contain a physical stabilizing system, such as a surfactant (ionic or nonionic), polymer (nonionic polymers, polyelectrolytes, or biopolymers), or mixtures thereof.

For embodiments in which the compound is provided in a suspension, the dosage form contains two phases. The continuous or external phase is generally a liquid or semi-solid while the dispersed or internal phase is made up of particulate matter that is essentially insoluble in, but dispersed throughout, the continuous phase. The insoluble matter may be intended for physiologic action, for example by external coating. Although the suspension system may separate on standing, the rate of settling may be decreased by varying the formulation to retain a sufficiently homogenous composition for at least the period of time necessary to administer the required dose after shaking its container.

The compound may also be administered in an aerosol, which depends on the power of compressed or liquefied gas to expel the contents from the container. Propellants in the container are responsible for developing the proper pressure within the container and it expel the product when the valve is opened and aids in the atomization or foam production of the products. Topical pharmaceuticals aerosols utilize hydrocarbon (propane, butane, and isobutene) and compressed gases such as nitrogen, carbon dioxide, and nitrous oxide.

Any of these dosage forms can contain separate reservoirs of compounds I/II and an adjunct agent (such as an agent for activating compound II to form compound I).

Example 7

Vitiligo Animal Models

This example describes the use of animal models to screen for treatments for vitiligo, including the selection of regimens for treatment, prevention and combination treatments. Animal models are used to test the claimed compounds, as well as combination formulations, such as those described herein. In particular examples, topical formulations that contain compounds I and/or II are applied to the skin of the animal and the therapeutic response is assessed. After the formulations are administered to the animal, the skin is examined for evidence of decreased number or size of depigmented areas.

The C57BL/6J Ler-vit/vit mouse strain has been beneficial as a vitiligo research tool (Lerner et al., *J. Invest. Dermatol.* 87(3):299-304 (September 1986)). This strain arose from the C57BL/6J strain. The vitiligo mouse has congenital dorsal and ventral white spots as well as replacement of pigmented hairs by white hairs. The lack of pigment is due to absence of melanocytes from the epidermis and hair follicles.

Another mouse model is the $C57BL/6\text{-}mi^{vit}/mi^{vit}$ mouse, which has a slowly progressing retinal degeneration with unevenly pigmented retinal pigment epithelium. See, e.g., Smith et al., *Invest. Ophthalmol. & Vis. Sci.* 35(10):3625-3632 (September 1994).

An alternative animal model is the Smyth line (SL) chicken developed by Dr. J. Robert Smyth, Jr. at the University of Massachusetts, Amherst, Mass. See, e.g., Shi et al., *BMC Immunol.* 13:18 (April 2012); Stepicheva et al., *J. Immunol.* 184:83.16 (2010).

In the model, the animal is exposed to the test agent, using different routes, dosages and regimens of administration. In particular examples, the drugs disclosed herein are applied topically to the areas that have been or will be tape stripped. Alternatively, the test drug is administered systemically. The drug is administered one or more times at fixed intervals prior to or following tape stripping (for example, daily following tape stripping or following the appearance of depigmented skin areas or depigmented hair patches). Drug response can be assessed by measuring such indicia of disease as the number, surface area or size of depigmented areas. Histological analysis of skin specimens is also performed to determine the number of melanocytes within the epidermis. Other histological findings may include an increased number of Langerhans' cells, epidermal vacuolization, thickening of the basement membrane, T-cell inflammatory infiltrate, and neural alterations (Montes et al., *Int. J. Dermatol.*, 42(1):57-61 (January 2003).) Deposits of extracellular granular material and/or foci of vacuolar degeneration of basal and parabasal keratinocytes may be observed (Moellmann et al., *J. Inv. Dermatol.* 79:312-330 (1982).) Inflammatory vitiligo may present with psoriasiform hyperplasia, parakeratotic mounds, acanthosis with elongation of rete ridges, and/or dilated vessels (Verma, *Dermatology Online Journal* 11(3):13 (2005).)

Example 8

Methods of Treatment and Combination Formulations

Subjects to be treated with the claimed formulations are selected based on a clinical and/or histopathological presentation of vitiligo. Subjects also may be selected based on an increased risk of developing vitiligo, such as a family history of vitiligo and/or presence of another disease associated with increased incidence of vitiligo. The claimed compositions are generally applied topically to the depigmented areas on the skin, although they may also be applied more generally to the skin or administered systemically. Treatment may be continued for at least a week, month, or year, and in some subjects treatment may extend over multiple years, the duration of disease, or the lifetime of the subject.

In particular cases, subjects are selected for concomitant treatment with other pharmaceutical or non-pharmaceutical interventions, such as systemic Plaquenil®, topical corticosteroid, phototherapy, psoralen photochemotherapy, or excimer laser therapy. In other cases the compounds I and/or II are administered with no other treatment for vitiligo.

In one example, the subject is selected by making a diagnosis of vitiligo. A therapeutically effective amount of the compound is provided in a topical petrolatum jelly formulation and the formulation is applied directly to depigmented areas, such as patches on the face and extremities. The pharmaceutical formulation is applied to the depigmented patches daily, for example 2-4 times per day for more than one day, for example at least one week. Topical application of the formulation to the depigmented areas is continued until the areas to which the formulation is applied show evidence of repigmentation or disappear, or their progression is delayed or stopped.

In other examples, the therapeutic compound is provided in an effective amount in a sunscreen formulation and is applied to the skin prior to exposure to ultraviolet radiation, to protect against exposure to ultraviolet radiation. The sunscreen formulation may contain, for example, an effective amount of PABA or zinc oxide to minimize skin exposure to ultraviolet radiation.

Combination therapies are also provided that combine the compounds of formula I and/or II (which includes salts thereof) with another agent that treats vitiligo or another condition. Combination formulations for the treatment of vitiligo may include combination formulations that include a topical corticosteroid, such as a Group I, II, III, IV, V, VI or VII corticosteroid, for example any of the following:

Group I (very potent: up to 600 times stronger than hydrocortisone)
    Clobetasol propionate 0.05% (Dermovate®)
    Betamethasone dipropionate 0.25% (Diprolene®)
    Halobetasol proprionate 0.05% (Ultravate®)
    Diflorasone diacetate 0.05% (Psorcon®)
Group II
    Fluocinonide 0.05% (Lidex®)
    Halcinonide 0.05% (Halog®)
    Amcinonide 0.05% (Cyclocort®)
    Desoximetasone 0.25% (Topicort®)
Group III
    Triamcinolone acetonide 0.5% (Kenalog®, Aristocort® cream)
    Mometasone furoate 0.1% (Elocon® ointment)
    Fluticasone propionate 0.005% (Cutivate®)
    Betamethasone dipropionate 0.05% (Diprosone®)
Group IV
    Fluocinolone acetonide 0.01-0.2% (Synalar®, Synemol®, Fluonid®)
    Hydrocortisone valerate 0.2% (Westcort®)
    Hydrocortisone butyrate 0.1% (Locoid®)
    Flurandrenolide 0.05% (Cordran®)
    Triamcinolone acetonide 0.1% (Kenalog®, Aristocort® A ointment)
    Mometasone furoate 0.1% (Elocon® cream, lotion)
Group V
    Triamcinolone acetonide 0.1% (Kenalog®, Aristocort® cream, lotion)
    Fluticasone propionate 0.05% (Cutivate® cream)
    Desonide 0.05% (Tridesilon®, DesOwen® ointment)
    Fluocinolone acetonide 0.025% (Synalar®, Synemol® cream)
    Hydrocortisone valerate 0.2% (Westcort® cream)
Group VI
    Prednicarbate 0.05% (Aclovate® cream, ointment)
    Triamcinolone acetonide 0.025% (Aristocort® A cream, Kenalog® lotion)
    Fluocinolone acetonide 0.01% (Capex® shampoo, Dermasmooth®)
    Desonide 0.05% (DesOwen® cream, lotion)
Group VII
    Hydrocortisone 2.5% (Hytone® cream, lotion, ointment)
    Hydrocortisone 1% (Many over-the-counter brands)

In some examples, the subject is diagnosed with a disorder in addition to vitiligo. For example, the subject presents with vitiligo and another pre-existing disorder, and is treated with the topical formulation that contains the compounds of formula I and/or II. The subject may be treated in combination or adjunctively with a therapeutic agent for the pre-existing disorder. If the pre-existing disorder is, for example, a thyroid disorder, the subject may be treated with thyroid hormone replacement.

In another example, a subject with vitiligo of the eye, or around the eye, may also be diagnosed with dry eyes and the combination therapy is administered to the subject. In one example, the subject is found to have a meibomitis that would be responsive to topical application of corticosteroids, such as a prednisolone acetate ophthalmic suspension 1%. The compounds of formula I and/or II (which includes salts thereof) are suspended in the prednisolone formulation and instilled in or applied to the eye 2 to 4 times a day. In other examples, if the dry eyes are associated with seasonal allergies or other inflammatory conditions, the eye drops are administered with or in a formulation that includes antihistamines (such as pheniramine, emedastine, or azelastine), decongestants (such as tetrahydrozoline hydrochloride or naphazoline), or a non-steroidal anti-inflammatory agent (such as nepafenac or ketorolac), corticosteroids (such as fluorometholone or loteprednol), mast cell stabilizers (such as azelastie, cromal, emedastine, ketotifen, lodoxamine, nedocromil, olopatadine, or pemirolast). If the dry eyes are associated with an infectious bacterial condition (such a meibomian gland infection or corneal infection) the eye drops are administered with or in a combination formulation can contain appropriate antibiotics (such as ciprofloxacin, erythromycin, gentamicin, ofloxacin, sulfacetamine, tobramycin, or monofloxacin). If the dry eyes are associated with a viral infection, the eye drops are administered with or in a combination formulation with an anti-viral agent such as trifluridine or idoxuridine.

Example 9

Topical Applicators and Dosage Forms

The compositions of the invention may be used in an application device that permits application of the composition to a target site on the skin without applying the composition to non-target site areas of the skin. For example, a device may be employed that allows the composition to be applied without first applying the composition to one's fingers. Suitable devices include spatulas, swabs, syringes without needles, and adhesive patches. Use of spatulas or swabs, or the like may require the device to be inserted into a container containing the composition. Using syringes or adhesive patches may be accomplished by filling the syringe or patch with the composition. The composition may then be topically spread by the spatulas or swabs, or may be expelled from the syringes onto the person's skin.

In one embodiment of the invention, the composition containing the compound and the enhancing agent is provided in an adhesive patch. Some examples of adhesive patches are well known. For example, see U.S. Pat. Nos. Des. 296,006; 6,010,715; 5,591,767; 5,008,110; 5,683,712; 5,948,433; and 5,965,154. Such patches generally have an adhesive layer, which is applied to a person's skin, a depot or reservoir for holding the pharmaceutical agent, and an exterior surface that prevents leakage of the pharmaceutical from the depot. The exterior surface of a patch is typically non-adhesive.

In accordance with the present invention, the compound for treating vitiligo is incorporated into the patch so that the compound remains stable for extended periods of time. The compound may be incorporated into a polymeric matrix that stabilizes it, and permits the compound to diffuse from the matrix and the patch. The compound may also be incorporated into the adhesive layer of the patch so that once the patch is applied to the skin the compound may diffuse on to the skin or even into or through the skin. In accordance with such an embodiment, the adhesive preferably comprises an enhancing agent, as disclosed herein. In one embodiment, the adhesive layer may be heat activated whereby temperatures of about 37° C. cause the adhesive to slowly liquefy so that the compound diffuses out of the patch and on to, into, or through the skin. The adhesive may remain tacky when stored at less than 37° C., and once applied to the skin, the adhesive loses its tackiness as it liquefies. The administration of the compound is complete once the patch no longer adheres to the skin.

Alternatively, the compound may be provided in one or more wells or pockets disposed near the surface of the patch that will contact the skin. In one embodiment, the compound is stored in the wells in a dried, or lyophilized state. Storing such patches in a cooled atmosphere (e.g., about 4° C.) maintains the stability of the compound. A patch may be removed from the cool atmosphere when needed, and applied to a person's skin where the compound may be solubilized upon mixing with fluid, such as water or saline. The fluid may be provided separately or as a component of the patch. For example, fluid may be provided on a person's skin so that when the patch containing the dried compound interacts with the fluid, the compound is exposed to the fluid and is solubilized. The solubilized compound may then be able to be absorbed by the skin. As another example, the patch may contain one or more wells or pockets to hold fluid in the patch. The fluid may be forced from the wells or pockets to cause the fluid to mix with the dried compound. For example, the fluid may be provided in a pocket in the patch, and in some embodiments contains an agent for enhancing or activating the compound. Pressure exerted on the patch causes the pocket to rupture and release the fluid so that it mixes with the dried compound. The composition containing the compound may thus diffuse out of the patch. In another example, a fluid such as a gel or creams that contains water may be applied to the skin at a target site. The patch containing the dried compound is then applied to the skin where the fluid mixes with the compound and the composition moves out of the patch and on to the skin.

In patches containing wells of dried compound, the wells are sealed so that the compound remains in the wells until the compound is administered. Accordingly, the wells are sealed with a membrane or film that prevents the compound from diffusing from the wells in the compound's dry state, but that permits the compound to diffuse from the wells when it is solubilized. The membrane may either be porous or nonporous. In one embodiment, the membrane comprises cellulose or starch, and more particularly, the membrane may contain polyvinyl alcohol, polyethylene oxide, and hydroxypropyl methyl cellulose. The membrane is thin (ranging in thickness from about 1 μm to about 1 mm) and dissolves upon contacting liquid. Thus, gel or cream placed on the person's skin or fluid directed from a pocket in the patch may contact the cellulose membrane and cause the membrane to dissolve. After dissolving, the fluid mixes with the dried compound and solubilizes the compound. The composition then diffuses out of the patch and on to the subject's skin.

Additionally, the transdermal patch may include a plurality of small needles that extend through the stratum corneum, but do not extend into the dermis to rupture blood vessels. The needles may be between 20 μm and 1 mm long when extending from the dermal surface of the patch. Thus, the needles extend through the stratum corneum, but terminate before the dermis where the capillary beds are located. The needles may be solid or hollow. Hollow needles may have a lumen extending along their length so that the composition can pass from the depot in the patch to the end of the needle in the epidermis. Solid needles may be used to permit the composition to diffuse along the outer surface of the needle into the epidermis.

In use, the topical applicator is adhesively applied to a target area of the skin that has one or more depigmented patches, and the applicator is left in place until the compound in the patch is administered. The topical applicator (such as a patch) provides sustained release of the drug over a prolonged period of time, such as several hours, or even at least a day or longer.

Example 10

Other Dosage Forms and Additives

The topical formulation may be prepared in a variety of forms. Solids are generally firm and non-pourable and commonly are formulated as a bar or stick, or in particulate form; solids may be opaque or transparent, and optionally may contain solvents (including water and alcohol), emulsifiers, moisturizers, emollients, fragrances, dyes/colorants, preservatives and active ingredients. Creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Lotions and creams also may optionally contain moisturizers and emollients (especially in the case of skin care products), as well as fragrances, dyes/colorants, preservatives and active ingredients. Gels/serums may be prepared with a range of viscosities, from thick (high viscosity) to thin (low viscosity) and differ principally from lotions and creams in that gels/serums are usually clear rather than opaque. Like lotions and creams, gels/serums often contain emulsifiers, solvents (including water and alcohol) and viscosity adjusters, and may also contain moisturizers and emollients, fragrances, dyes/colorants, preservatives and active ingredients. Aqueous liquids are thinner than creams, lotions or gels, and are generally transparent; liquids usually do not contain emulsifiers. Liquid topical products often contain other solvents in addition to water (including alcohol) and may also contain viscosity adjusters, moisturizers and emollients, fragrances, dyes/colorants/pigments, preservatives and active ingredients.

Suitable emulsifiers for use in the formulations include, but are not limited to, Incroquat™ Behenyl TMS (behentrimonium methosulfate, cetearyl alcohol), non-ionic emulsifiers like polyoxyethylene oleyl ether, PEG-40 stearate, ceteareth-12 (e.g., Eumulgin® B-1 manufactured by Henkel), ceteareth-20 (e.g., Eumulgin® B-2 manufactured by Henkel), ceteareth-30, Lanette O (manufactured by Henkel; ceteareth alcohol), glyceryl stearate (e.g., Cutina® GMS manufactured by Henkel), PEG-100 stearate, Arlacel™ 165 (glyceryl stearate and PEG-100 stearate), steareth-2 and steareth-20, or combinations/mixtures thereof, as well as cationic emulsifiers like stearamidopropyl dimethylamine and behentrimonium methosulfate, or combinations/mixtures thereof. In addition, cationic emulsifiers are preferably combined or mixed with non-ionic emulsifiers in order to form stable emulsion product forms containing high strontium salt concentrations.

Suitable secondary active ingredients for use in the formulations include, but are not limited to, alpha hydroxy acids, sunscreens, antiperspirants, anti-acne drugs, vitamins (especially vitamins A and C) and minerals, and various prescription and over-the-counter medications. The compositions disclosed herein can have multiple active ingredients within the same topical formulation, and combinations of active ingredients such as those listed above may be used, as appropriate for the condition or conditions being treated.

Suitable fragrances and colors, such as FD&C Red No. 40 and FD&C Yellow No. 5, may be used in the formulations of the present invention. Other examples of fragrances and colors suitable for use in topical products are known in the art.

Other suitable additional and adjunct ingredients which may be included in the formulations include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., *CTFA Cosmetic Ingredient Handbook*, 2nd edition, eds. John A. Wenninger and G. N. McEwen, Jr. (CTFA, 1992).

Also, a variety of product types, including cosmetics, may be formulated in each of the forms described above (i.e., solids, creams, lotions, gels, and liquids). For example, cleansers (for face and body), shampoos/conditioners, hair treatments/dyes/perms/straighteners, antiperspirants/deodorants, make-up products, and other facial, hand and body products may be formulated in any of the five major product forms: solids, creams, lotions, gels, or liquids. Common solid form products include cosmetics such as lipsticks, blushes and rouges, makeup products, antiperspirant and deodorant sticks, and cleansers such as bar soap and powder detergents. Other examples of solid form products include lozenges and suppositories for the treatment of cutaneous lupus lesions of the mucous membranes (such as the mouth or anus). Common cream and lotion form products include alpha-hydroxy acid (AHA) products, moisturizing products and sunscreens, shampoos/conditioners and other hair care products, and cosmetics like concealers and foundations. Common gel products include shaving gels and aftershaves. Common liquid form products include anti-acne solutions, aftershaves, gargles/mouthwashes, and toners/bracers/skin conditioners.

Other methodologies and materials for preparing formulations in a variety of forms are also described in Anthony L. L. Hunting (ed.), "A Formulary of Cosmetic Preparations (Vol. 2)—Creams, Lotions and Milks," Micelle Press (England, N.J. 1993). See, for example, Chapter 7, pp. 5-14 (oils and gels); Chapter 8, pp. 15-98 (bases and emulsions); Chapter 9, pp. 101-120 ("all-purpose products"); Chapter 10, pp. 121-184 (cleansing masks, creams, lotions); Chapter 11, pp. 185-208 (foundation, vanishing and day creams); Chapter 12, pp. 209-254 (emollients); Chapter 13, pp. 297-324 (facial treatment products); Chapter 14, pp. 325-380 (hand products); Chapter 15, pp. 381-460 (body and skin creams and lotions); and Chapter 16, pp. 461-484 (baby products); the contents of which are incorporated herein by reference.

Example 11

An Exemplary Topical Formulation

The topical formulation may be prepared in a variety of strengths and using a variety of excipient concentrations as described herein. Table 3 is a list of the excipients used in this example, and without being limited to any particular theory, the function of each excipient.

TABLE 3

| Excipient | Function |
| --- | --- |
| PEG400, Glycofurol | Solvent |
| PEG8000, PEG4500, PEG3350 | Topical Base |

TABLE 3-continued

| Excipient | Function |
| --- | --- |
| Tefose ® 63, Span ®, Myrj ®, TPGS | Surfactant |
| DMI, PG | Penetration enhancer |
| H$_2$O | Emollient |
| BHT | Antioxidant |
| Caramel | Color Additive |

With reference to Table 3, PEG400 employed in working examples was Super Refined Polyethylene Glycol 400, commercially available from Croda Inc., Edison N.J. Likewise, Super Refined dimethyl isosorbide (DMI), also available from Croda Inc. typically was used in these examples.

To prepare the formulations, excipients and compound I was added to a glass container, and heated and/or sonicated at 65° C. to 70° C. to dissolve API completely. The sample is then cooled to room temperature. The ingredients for two exemplary formulations prepared by this method are set forth below in Tables 4 and 5.

TABLE 4

| Component | Grade | Weight % | Weight (g) per kg |
| --- | --- | --- | --- |
| Compound I | GMP | 3.0 | 30 |
| Super Refined Polyethylene Glycol 400 | NF | 39.95 | 399.5 |
| Polyethylene Glycol 4500 | NF | 32.0 | 320 |
| Butylated Hydroxytoluene, Granular | NF | 1.0 | 10 |
| MYRJ S100-PA-SG | — | 5.0 | 50 |
| Super Refined Dimethyl Isosorbide | — | 15.0 | 150 |
| Purified Water | USP | 4.0 | 40 |
| Caramel | NF | 0.05 | 0.5 |
| Total | | 100 | 1000 |

TABLE 5

| Component | Grade | Weight % | Weight (g) per kg |
| --- | --- | --- | --- |
| Compound I | GMP | 6.0 | 60 |
| Super Refined Polyethylene Glycol 400 | NF | 33.95 | 339.5 |
| Polyethylene Glycol 4500 | NF | 35.0 | 350 |
| Butylated Hydroxytoluene, Granular | NF | 1.0 | 10 |
| MYRJ S100-PA-SG | — | 5.0 | 50 |
| Super Refined Dimethyl Isosorbide | — | 15.0 | 150 |
| Purified Water | USP | 4.0 | 40 |
| Caramel | NF | 0.05 | 0.5 |
| Total | | 100 | 1000 |

I claim:

1. A method of treating vitiligo, comprising administering to a subject a topical formulation comprising from 0.1% to 10% (w/w) of a compound

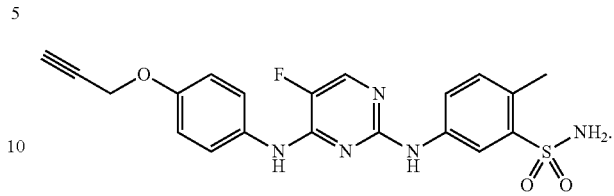

or a hydrate, a solvate, an N-oxide, or a pharmaceutically acceptable salt thereof.

2. The method of claim 1, wherein the subject is identified as having vitiligo.

3. The method of claim 1, wherein the subject is identified as being at risk of developing vitiligo.

4. The method of claim 1, wherein administering the topical formulation comprises administering a therapeutically effective amount of from about 0.0001 mg/kg/day to about 100 mg/kg/day.

5. The method of claim 1, wherein the topical formulation comprises from 0.2% to 6% (w/w) of the compound.

6. The method of claim 1, wherein the topical formulation comprises 3% (w/w) of the compound.

7. The method of claim 1, wherein the topical formulation comprises 6% (w/w) of the compound.

8. The method of claim 5, wherein the formulation comprises 30% to 40% (w/w) polyethylene glycol with an average molecular weight of from 4000 to 5000 Daltons.

9. The method of claim 1, wherein the subject has one or more depigmented skin areas, and the method comprises administering the compound topically to at least one of the depigmented skin areas.

10. The method of claim 5, further comprising administering the compound systemically to the subject.

11. The method of claim 1, comprising administering the compound systemically to the subject.

12. The method of claim 1, wherein the subject has vitiligo of the eye, and the compound ocularly to the patient.

13. The method of claim 1, comprising administering the compound either in combination or adjunctively with a second therapeutic.

14. The method of claim 11, wherein the second therapeutic is an anti-inflammatory, an antihistamine, an antibiotic, an antiviral medication, systemic phototherapy, psoralen photochemotherapy, excimer laser therapy, thyroid hormone replacement medication, or any combination thereof.

* * * * *